US012369836B2

(12) United States Patent
Aranda Hernandez et al.

(10) Patent No.: US 12,369,836 B2
(45) Date of Patent: Jul. 29, 2025

(54) PROPAGATION PATTERNS METHOD AND RELATED SYSTEMS AND DEVICES

(71) Applicant: Medtronic, Inc., Minneapolis, MN (US)

(72) Inventors: Alfonso Aranda Hernandez, Maastricht (NL); Subham Ghosh, Blaine, MN (US); Joshua J. Blauer, White Bear Lake Township, MN (US)

(73) Assignee: Medtronic, Inc., Minneapolis, MN (US)

( * ) Notice: Subject to any disclaimer, the term of this patent is extended or adjusted under 35 U.S.C. 154(b) by 269 days.

(21) Appl. No.: 16/706,928

(22) Filed: Dec. 9, 2019

(65) Prior Publication Data

US 2020/0196892 A1    Jun. 25, 2020

Related U.S. Application Data

(60) Provisional application No. 62/782,764, filed on Dec. 20, 2018.

(51) Int. Cl.
| | |
|---|---|
| *A61N 1/08* | (2006.01) |
| *A61B 5/00* | (2006.01) |
| *A61B 5/282* | (2021.01) |
| *A61B 5/327* | (2021.01) |
| *A61B 5/339* | (2021.01) |

(Continued)

(52) U.S. Cl.
CPC .............. *A61B 5/341* (2021.01); *A61B 5/282* (2021.01); *A61B 5/327* (2021.01); *A61B 5/339* (2021.01); *A61B 5/6805* (2013.01); *A61B 5/6831* (2013.01); *A61N 1/36507* (2013.01); *A61N 1/371* (2013.01); *A61N 1/3756* (2013.01)

(58) Field of Classification Search
CPC ................................ A61B 5/341; A61B 5/349
See application file for complete search history.

(56) References Cited

U.S. PATENT DOCUMENTS

| 6,980,675 B2 | 12/2005 | Evron et al. |
| 7,286,866 B2 | 10/2007 | Okerlund et al. |

(Continued)

FOREIGN PATENT DOCUMENTS

CN      106073753 A     11/2016

OTHER PUBLICATIONS (PCT/US2019/066234) Written Opinion of the International Searching Authority and Transmittal of the International Search Report, Mailed Apr. 14, 11 pages.

*Primary Examiner* — Michael J D'Abreu
(74) *Attorney, Agent, or Firm* — Mueting Raasch Group

(57) ABSTRACT

Methods and related systems and devices for cardiac therapy use pseudo-electric vectors (PEVs) for characterizing and representing the electrical forces generated by a patient's heart in a three-dimensional (3D) manner. PEVs may be used to predict whether a patient will respond to pacing therapy prior to implant, during implant, or in the follow-up after implant. Various cardiac therapy systems and devices, such as an electrocardiogram (ECG) belt or vest, which may include a plurality of external electrodes, may be used to obtain electrical activity information to generate the PEVs. One or more spatio-temporal PEVs may be determined using one or more sensors at one or more points in time. Spatial representation data may be determined based on the PEVs.

28 Claims, 16 Drawing Sheets

(51) Int. Cl.
    *A61B 5/341*     (2021.01)
    *A61N 1/365*     (2006.01)
    *A61N 1/37*     (2006.01)
    *A61N 1/375*     (2006.01)

(56) References Cited

U.S. PATENT DOCUMENTS

| | | |
|---|---|---|
| 7,308,297 B2 | 12/2007 | Reddy et al. |
| 7,308,299 B2 | 12/2007 | Burrell et al. |
| 7,321,677 B2 | 1/2008 | Evron et al. |
| 7,346,381 B2 | 3/2008 | Okerlund et al. |
| 7,454,248 B2 | 11/2008 | Burrell et al. |
| 7,499,743 B2 | 3/2009 | Vass et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,613,500 B2 | 11/2009 | Vass et al. |
| 7,742,629 B2 | 6/2010 | Zarkh et al. |
| 7,747,047 B2 | 6/2010 | Okerlund et al. |
| 7,778,685 B2 | 8/2010 | Evron et al. |
| 7,778,686 B2 | 8/2010 | Vass et al. |
| 7,813,785 B2 | 10/2010 | Okerlund et al. |
| 7,996,063 B2 | 8/2011 | Vass et al. |
| 8,060,185 B2 | 11/2011 | Hunter et al. |
| 8,401,616 B2 | 3/2013 | Verard et al. |
| 2003/0083586 A1 | 5/2003 | Ferek-Petric |
| 2003/0083587 A1 | 5/2003 | Ferek-Petric |
| 2004/0111021 A1* | 6/2004 | Olson .............. A61B 5/341 600/407 |
| 2005/0008210 A1 | 1/2005 | Evron et al. |
| 2006/0074285 A1 | 4/2006 | Zarkh et al. |
| 2011/0112398 A1 | 5/2011 | Zarkh et al. |
| 2011/0118616 A1* | 5/2011 | Vajdic .............. A61B 5/341 600/509 |
| 2013/0116739 A1 | 5/2013 | Brada et al. |
| 2014/0323882 A1 | 10/2014 | Ghosh et al. |
| 2014/0323892 A1 | 10/2014 | Ghosh et al. |
| 2014/0371832 A1 | 12/2014 | Ghosh |
| 2014/0371833 A1 | 12/2014 | Ghosh et al. |
| 2017/0340887 A1 | 11/2017 | Engels et al. |
| 2019/0290909 A1 | 9/2019 | Ghosh et al. |

\* cited by examiner

PROPAGATION PATTERNS METHOD AND RELATED SYSTEMS AND DEVICES

The present technology is generally related to methods and related systems and devices for cardiac therapy.

The cardiac conduction system includes the sinus atrial (SA) node, the atrioventricular (AV) node, the bundle of His, bundle branches and Purkinje fibers. A heartbeat is initiated in the SA node, which may be described as the natural "pacemaker" of the heart. An electrical impulse arising from the SA node causes the atrial myocardium to contract. The electrical impulse, or electrical pulse or signal, is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Patients with a conduction system abnormality, such as poor AV node conduction or poor SA node function, may receive an implantable medical device (IMD), such as a pacemaker, to restore a more normal heart rhythm and AV synchrony. Some types of IMDs, such as cardiac pacemakers, implantable cardioverter defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart, and control the delivery of therapeutic stimulation to the heart based on the sensing.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP) can be used to treat ventricular tachycardia (VT) to terminate substantially many monomorphic fast rhythms.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in the right and left ventricles of the heart. Significant differences in the timing of contractions can reduce cardiac efficiency. CRT, delivered by an IMD to the heart, may enhance cardiac output by resynchronizing the electromechanical activity of the ventricles of the heart. CRT may include "triple-chamber pacing" when pacing the right atrium, right ventricle (RV), and left ventricle (LV).

CRT is typically applicable to patients with abnormal impulse conduction through the ventricles such as left bundle branch block (LBBB). CRT is generally considered a successful heart failure (HF) therapy. However, about 30% of patients do not have a significant response effect to CRT. Attempting CRT may include irreversible implantation of a costly device and pacing electrodes during an invasive surgical procedure. Improper lead placement or insufficient programming of an IMD may contribute to unsuccessful attempts to provide CRT.

SUMMARY

The techniques of this disclosure generally relate to methods and related systems and devices for cardiac therapy, such as single-chamber or multiple chamber pacing (e.g., dual- or triple-chamber pacing), atrioventricular synchronous pacing, asynchronous pacing, triggered pacing, cardiac resynchronization pacing or therapy, or tachycardia-related therapy. This disclosure provides techniques that use pseudo-electric vectors (PEVs) for characterizing and representing the electrical forces generated by a patient's heart in a three-dimensional (3D) manner, which may be used to understand propagation patterns of the patient's heart. For example, electrical dyssynchrony of the heart may be evaluated using pseudo-electric vectors. In some cases, pseudo-electric vectors may be used to predict whether a patient will respond to pacing therapy prior to implant, during implant, or in the follow-up after implant. Techniques of the present disclosure may be used with various cardiac therapy systems and devices, such as an electrocardiogram (ECG) belt or vest, which may include a plurality of external electrodes.

In one aspect, the present disclosure relates to a cardiac sensing system including electrode apparatus having a plurality of external electrodes to sense electrical activity from tissue of a patient and computing apparatus having processing circuitry operatively coupled to the electrode apparatus. The processing circuitry is configured to: sense electrical activity using the plurality of external electrodes; determine a pseudo-electric vector for one or more of the external electrodes based on an estimated center of the patient's heart and the sensed electrical activity; and generate spatial representation data of the sensed electrical activity based on the one or more determined pseudo-electric vectors.

In another aspect, the present disclosure relates to a method including sensing electrical activity of a patient's heart using a plurality of external electrodes; determining a pseudo-electric vector for one or more of the external electrodes based on an estimated center of the patient's heart and the sensed electrical activity; and generating spatial representation data of the sensed electrical activity based on the one or more the determined pseudo-electric vectors.

In another aspect, the present disclosure relates to a system including interface circuitry configured to receive electrical activity information measured by a plurality of external electrodes that represents sensed electrical activity from tissue of a patient and processing circuitry operatively coupled to the interface circuitry. The processing circuitry is configured to: receive the electrical activity information; determine a pseudo-electric vector for one or more of the external electrodes based on an estimated center of the patient's heart and the received electrical activity information; and generate spatial representation data of the electrical activity information based on the one or more determined pseudo-electric vectors.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
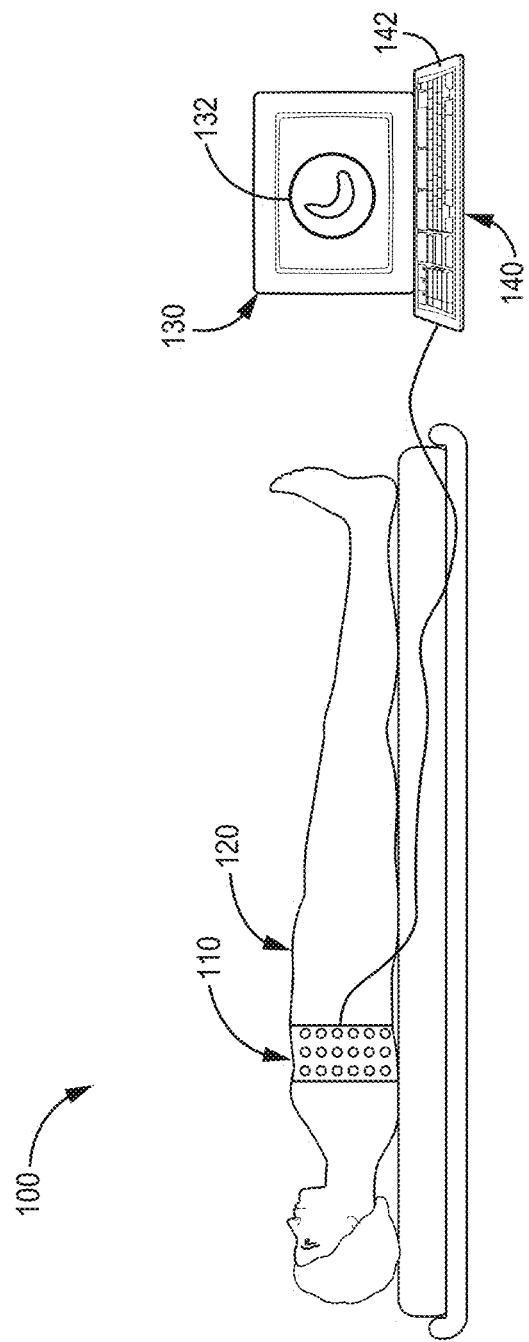
FIG. 1 is a diagram of an illustrative system including electrode apparatus, display apparatus, and computing apparatus for use with, e.g., the illustrative methods of FIGS. 14-15.

The techniques of this disclosure generally relate to methods and related systems and devices for cardiac therapy, such as single-chamber or multiple chamber pacing (e.g., dual- or triple-chamber pacing), atrioventricular synchronous pacing, asynchronous pacing, triggered pacing, cardiac resynchronization pacing or therapy, or tachycardia-related therapy. Although reference is made herein to implantable medical devices, such as a pacemaker, the methods and techniques may be used with any medical devices or systems related to a patient's heart. Various other applications will become apparent to one of skill in the art having the benefit of the present disclosure.

It may be beneficial to provide a technique for capturing and effectively visualizing propagation patterns of the patient's heart to detect electrical dyssynchrony and provide information that may be helpful to locate a lead or program a medical device. It may also be beneficial to provide a technique that uses fewer computational resources, such as processing and memory resources, then existing techniques. It may further be beneficial to provide a technique that uses less complicated equipment than existing techniques.

As used herein, the term "capture" generally refers to obtaining information or data, for example, related to imaging. The term "capture" in the context of pacing (e.g., effective capture of the heart from pacing) refers to determining whether a desired response is sensed in response to stimuli, such as sensing desirable electrical activity in response to electrical pulses delivered to a portion of the heart.

As used herein, the term "effective" generally refers to meeting conditions that would be sufficient to a person of ordinary skill in the art for performing a particular function. For example, effective pacing of the left ventricle may result in capture of the left ventricle when electrical or mechanical activity of the left ventricle is sensed and determined to provide cardiac therapy as desired.

The present disclosure provides propagation patterns techniques that use pseudo-electric vectors (PEVs) for characterizing and representing the electrical forces generated by the patient's heart in a three-dimensional (3D) manner. These techniques may be used to measure the magnitude and direction of the electrical forces generated by the heart at one or more points in time. Electrical dyssynchrony of the heart may be evaluated using pseudo-electric vectors, for example, without using computed tomography (CT) scan and/or without calculating an inverse solution. In some cases, pseudo-electric vectors may be used to predict whether a patient will respond to pacing therapy prior to implant, during implant, and in the follow-up after implant. For example, the effectiveness of CRT may be predicted based on information derived from pseudo-electric vectors. Before implantation, pseudo-electric vectors may be used to select patients as candidates for CRT and to determine what pacing may be available for CRT. During implantation, pseudo-electric vectors may be used to locate the lead and to program of the implantable medical device, which may reduce procedure time in some cases. After implantation, the device may be reprogrammed. Techniques of the present disclosure may be used with various cardiac therapy systems and devices, such as an electrocardiogram (ECG) belt or vest, which may include a plurality of external electrodes or a reduced set of external electrodes. The electrodes may be used to sense electrical activity, which may be used to calculate one or more pseudo-electric vectors.

In general, electrical or mechanical activity may be sensed, determined, acquired, or monitored using various techniques available to one having ordinary skill in the art who has the benefit of the present disclosure. As used herein, the term "monitoring" generally refers to sensing, acquiring, or receiving data or information that may be used, for example, being processed or stored.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 depicts an illustrative system 100 including electrode apparatus 110, display apparatus 130, and computing apparatus 140, which may be used with the propagation patterns technique of the present disclosure. The illustrative system 100 may be described as a cardiac sensing system. The electrode apparatus 110 as shown includes a plurality of electrodes incorporated, or included, within a band wrapped around the chest, or torso, of a patient 120. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Illustrative electrode apparatus may be described in U.S. Pat. No. 9,320,446 entitled "Bioelectric Sensor Device and Methods" and issued on Apr. 26, 2016, which is incorporated herein by reference in its entirety. Further, illustrative electrode apparatus 110 will be described in more detail in reference to FIGS. 2-3.

Although not described herein, the illustrative system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the illustrative systems, methods, and interfaces described herein may further use imaging apparatus to provide noninvasive assistance to a user (e.g., a physician) to calibrate and/or deliver cardiac pacing therapy, to locate and position a device to deliver cardiac pacing therapy, and/or to locate or select a pacing electrode or pacing vector proximate the patient's heart for pacing therapy in conjunction with the evaluation of pacing therapy.

For example, the illustrative systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a paced setting is optimal or determining whether one or more selected parameters are optimal, such as selected location information (e.g., location information for the electrodes to target a particular location). Illustrative systems and methods that use imaging apparatus and/or electrode apparatus may be described in U.S. Patent Publication No. 2014/0371832 filed on Jun. 12, 2013, and entitled "Implantable Electrode Location Selection." U.S. Patent Publication No. 2014/0371833 filed on Jun. 12, 2013, and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical-Electrical Vectors," each of which is incorporated herein by reference in its entirety.

Illustrative imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the patient's heart) within the heart or other areas of interest.

Systems and/or imaging apparatus that may be used in conjunction with the illustrative systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of one or more of mechanical cardiac functionality and electrical cardiac functionality (e.g., mechanical cardiac functionality only, electrical cardiac functionality only, or both mechanical cardiac functionality and electrical cardiac functionality), etc. The display 130 is used to display images either in real-time or images called up from the memory. Cardiac information may include, e.g., electrical heterogeneity information or electrical dyssynchrony information, surrogate electrical activation information or data, etc. that is generated using electrical signals gathered, sensed, or collected, using the electrode apparatus 110. This data may be processed (either in real time or after storage and retrieval) using any suitable EKG-gated reconstruction technique to form an image dataset or stream. This data can be visualized (i.e., displayed) on an operator console or workstation and further processed on an analysis/review workstation. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for calibrating and/or delivering pacing therapy, e.g., based on at least a heartrate, for driving a graphical user interface configured to noninvasively assist a user in targeting placement of a pacing device, and/or for evaluating pacing therapy at that location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 for performing the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of a leadless pacing device used to calibrate and/or deliver pacing therapy, e.g., based on at least a measured heartrate, graphical depictions of a leadless pacing device being positioned or placed to provide pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more illustrative methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the illustrative systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform the functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the illustrative systems, methods, and/or interfaces may be implemented using a computer readable storage medium, configured with a computer program, where the storage medium so configured causes the computer to operate in a specific and predefined manner to perform functions described herein. Further, in at least one embodiment, the illustrative systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
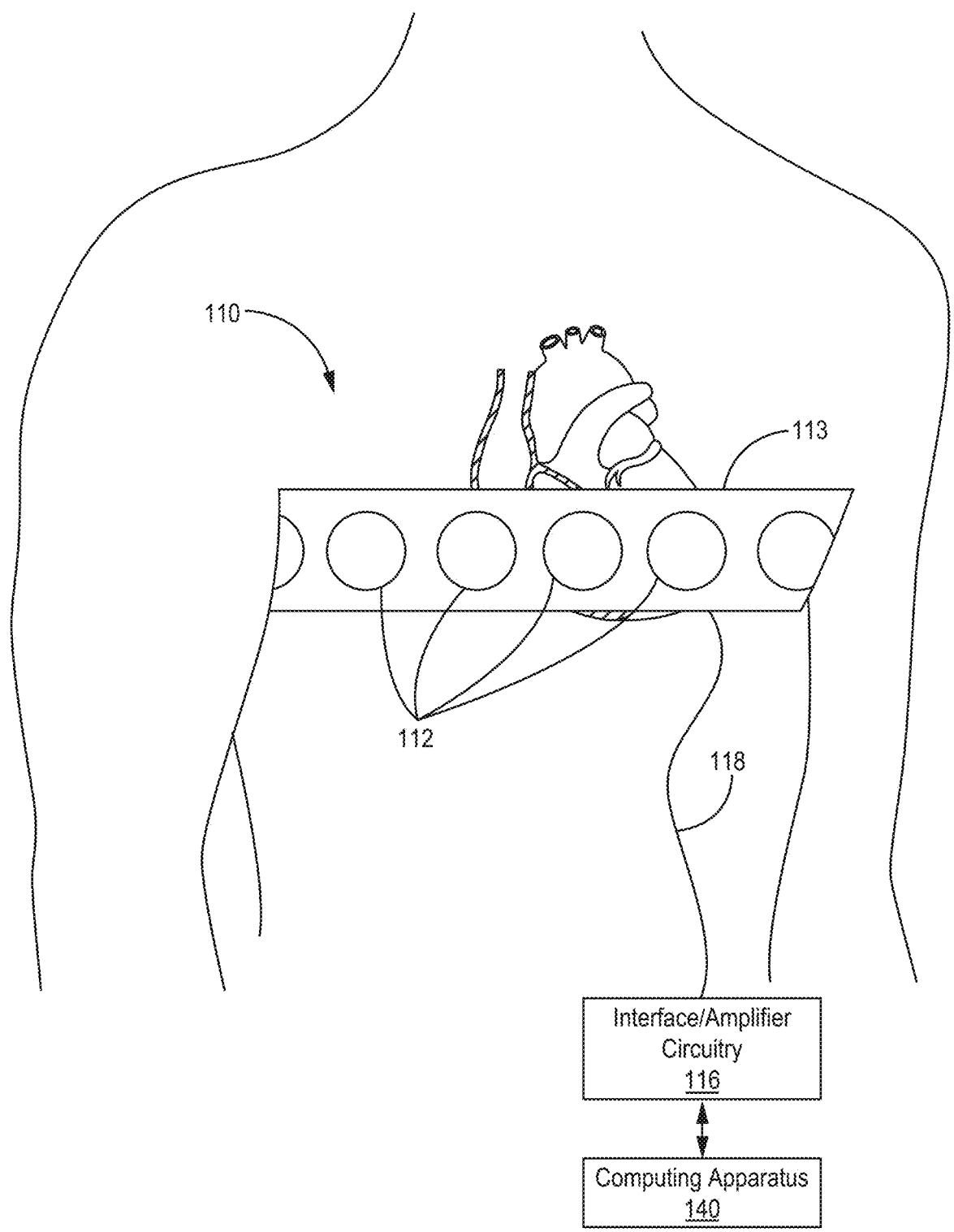
FIGS. 2-3 are diagrams of illustrative external electrode apparatus for measuring torso-surface potentials for use with, e.g., the illustrative methods of FIGS. 14-15.
Figure 3:
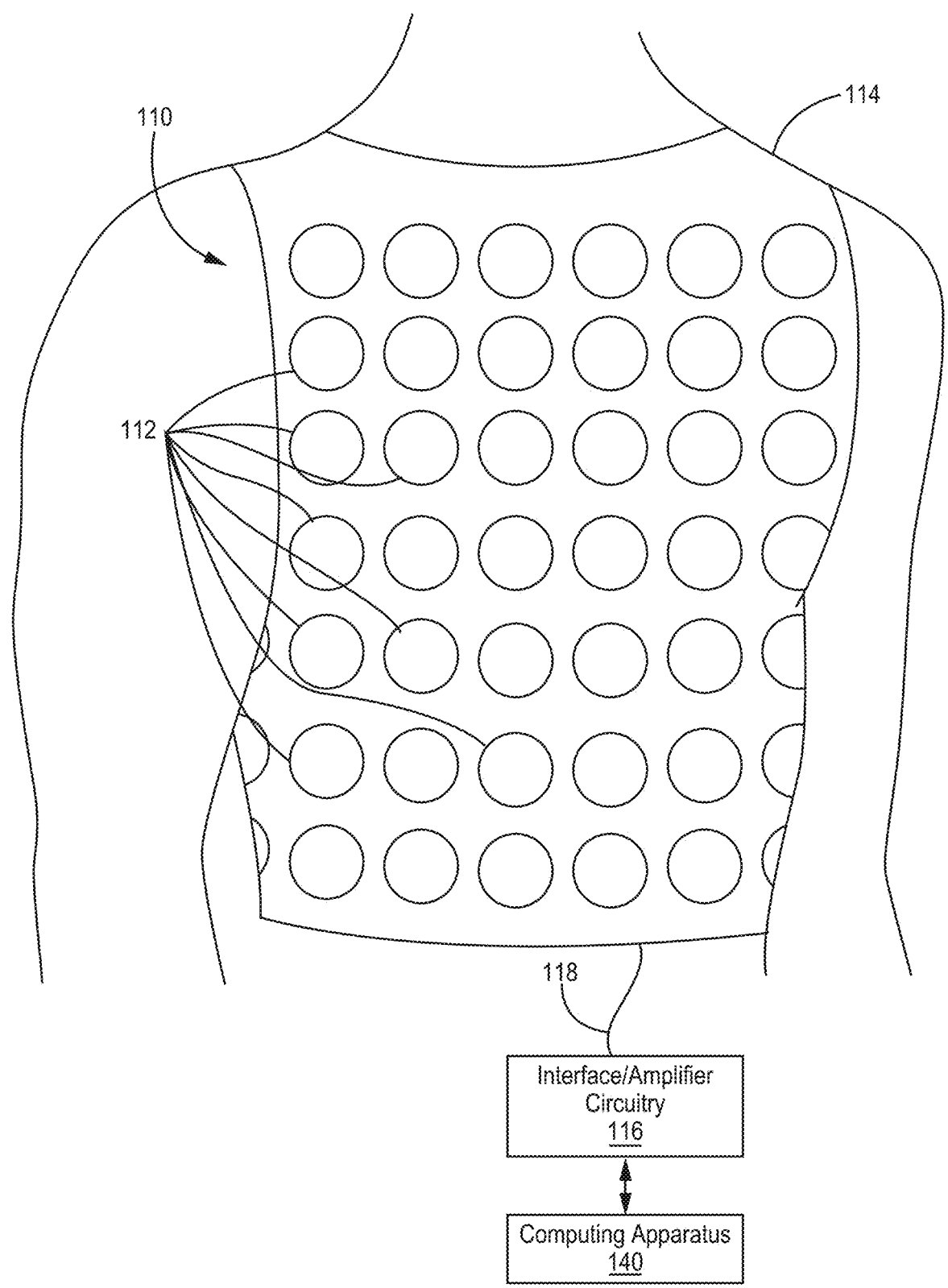

Electrical activation times of the patient's heart may be useful to evaluate a patient's cardiac condition and/or to calibrate, deliver, or evaluate cardiac therapy to be or being delivered to a patient. Surrogate electrical activation information or data of one or more regions of a patient's heart may be sensed, or determined, using electrode apparatus 110 as shown in FIGS. 1-3. The illustrative electrode apparatus 110 may be configured to measure body-surface potentials of a patient 120 and, more particularly, torso-surface potentials of a patient 120.

As shown in FIG. 2, the illustrative electrode apparatus 110 may include a set, or array, of electrodes 112, a strap 113, and interface/amplifier circuitry 116. In at least one embodiment, a portion of the set of electrodes may be used wherein the portion corresponds to a particular location on the patient's heart. The electrodes 112 may be attached, or coupled, to the strap 113, and the strap 113 may be configured to be wrapped around the torso of a patient 120 such that the electrodes 112 surround the patient's heart. As further illustrated, the electrodes 112 may be positioned around the circumference of a patient 120, including the posterior, lateral, posterolateral, anterolateral, and anterior locations of the torso of a patient 120.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other illustrative systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc. In some embodiments, the interface/amplifier circuitry 116 may be described as being part of the computing apparatus 140.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 120. Further, in other examples, electrodes 112 (e.g., arranged in an array) may be part of, or located within, patches, vests, and/or other manners of securing the electrodes 112 to the torso of the patient 120.

The electrodes 112 may be configured to surround the heart of the patient 120 and record, or sense, the electrical signals associated with the depolarization and repolarization of the heart after the signals have propagated through the torso of a patient 120. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of the patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. The computing apparatus 140 may be configured to analyze the signals from the electrodes 112 to provide as anterior-septal electrode signals and surrogate cardiac electrical activation times, e.g., representative of actual, or local, electrical activation times of one or more anterior-septal regions of the patient's heart, as will be further described herein, e.g., for use in calibrating, delivering, and/or evaluating pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Illustrative systems, methods, and/or interfaces may noninvasively use the electrical information collected using the electrode apparatus 110 to evaluate a patient's cardiac condition and/or to calibrate, deliver, or evaluate pacing therapy to be or being delivered to the patient.

FIG. 3 illustrates another illustrative electrode apparatus 110 that includes a plurality of electrodes 112 configured to surround the heart of the patient 120 and record, or sense, the electrical signals associated with the depolarization and repolarization of the heart after the signals have propagated through the torso of the patient 120. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times.

Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 120, including, for example, the anterior, lateral, posterolateral, anterolateral, and posterior surfaces of the torso of the patient 120.

The vest 114 may be formed of fabric with the electrodes 112 attached to the fabric. The vest 114 may be configured to maintain the position and spacing of electrodes 112 on the torso of the patient 120. Further, the vest 114 may be marked to assist in determining the location of the electrodes 112 on the surface of the torso of the patient 120. In one or more embodiments, the vest 114 may include about 17 or more anterior electrodes positionable proximate the anterior torso of the patient, and about 39 or more posterior electrodes positionable proximate the anterior torso of the patient. In some examples, there may be about 25 electrodes 112 to about 256 electrodes 112 distributed around the torso of the patient 120, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 112, and not the entire set, can be used to generate activation times corresponding to a particular location of the patient's heart that the portion of the set of electrodes corresponds to.

The illustrative systems, methods, and interfaces may be used to provide noninvasive assistance to a user in the evaluation of a patient's cardiac health or status, and/or the evaluation of cardiac therapy such as pacing therapy by use of the electrode apparatus 110 (e.g., cardiac therapy being presently-delivered to a patient during implantation or after implantation). Further, the illustrative systems, methods, and interfaces may be used to assist a user in the configuration, or calibration, of the cardiac therapy, such as pacing therapy, to be or being delivered to a patient (e.g., based on a measured heartrate).

Electrical activity may be sensed using a plurality of external electrodes, such as electrodes 112 of FIGS. 1-3. The electrical activity can be sensed by a plurality of electrodes during pacing therapy or in the absence of pacing therapy. The sensed electrical activity can be used to evaluate pacing therapy to a patient. The electrical activity sensed using the ECG belt described can be used to evaluate at least one paced setting of the pacing therapy on the heart. As an example, a paced setting can be any one parameter or a combination of parameters including, but not limited to, electrode position, pacing polarity, pacing output, pacing pulse width, timing at which pacing is delivered relative to atrial (A) or ventricular (V) timing, pacing rate, etc.

Further, body-surface isochronal maps of ventricular activation can be constructed using the sensed electrical activity during pacing therapy or in the absence of pacing therapy. The sensed electrical activity and/or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of pacing therapy at one or more paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In at least one embodiment, only ASAT may be determined and further used, and/or ASAT may be more heavily weighted than other values.

One or more paced settings associated with the pacing therapy may be evaluated. A paced setting can include a plurality of pacing parameters. The plurality of pacing parameters can be optimal if the patient's cardiac condition improves, if the pacing therapy is effectively capturing a desired portion of the patient's heart, and/or if a metric of electrical heterogeneity improves by a certain threshold compared to a baseline rhythm or therapy. In at least one embodiment, the determination of whether the paced setting is optimal can be based on at least one metric of electrical heterogeneity generated from electrical activity during pacing (and also, in some embodiments, during native conduction, or in the absence of pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, and/or if the location of the pacing therapy to excite one or more portion of the patient's heart causes a particular pattern of excitation of the muscle fibers in the heart. In addition, the plurality of pacing parameters can be optimal if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is optimal. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is may be optimal.

The paced setting can be determined to be optimal in response to the pacing therapy using the paced setting being acceptable, being beneficial, being indicative of complete engagement of patient's native cardiac conduction system, being indicative of correction of a ventricular conduction disorder (e.g., left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the pacing therapy, etc. The pacing location can refer to the location of any of the one or more pacing electrodes that are positioned using a lead, a leadless device, and/or any device or apparatus configured to deliver.

A paced setting for pacing therapy may be adjusted. In at least one embodiment, the paced setting can be adjusted in response to the paced setting being not optimal. In at least one embodiment, the paced setting can be adjusted in response to the paced setting being within an optimal range but in order to determine whether the paced setting can be at a position within the optimal range that is more beneficial, more useful, more functional, etc., for the pacing therapy. The paced setting could be adjusted to find the most optimal metric of electrical heterogeneity.

In one or more embodiments, a determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

Various techniques for utilizing an electrode apparatus having a plurality of external electrodes to sense electrical activity from tissue of a patient that may be used with the devices, systems, and methods described herein are disclosed in U.S. patent application Ser. No. 15/934,517, filed 23 Mar. 2018, entitled "Evaluation of Ventricle from Atrium Pacing Therapy," which is incorporated herein by reference in its entirety.

In general, the computing apparatus 140 may be operatively coupled to the electrode apparatus 113 or 114 and configured to use pseudo-electric vectors (PEVs) to generate spatial representation data based on sensed electrical activity from the electrode apparatus 113 or 114. Each PEV may contain spatio-temporal information that may be used to provide the spatial representation data.

Figure 4:
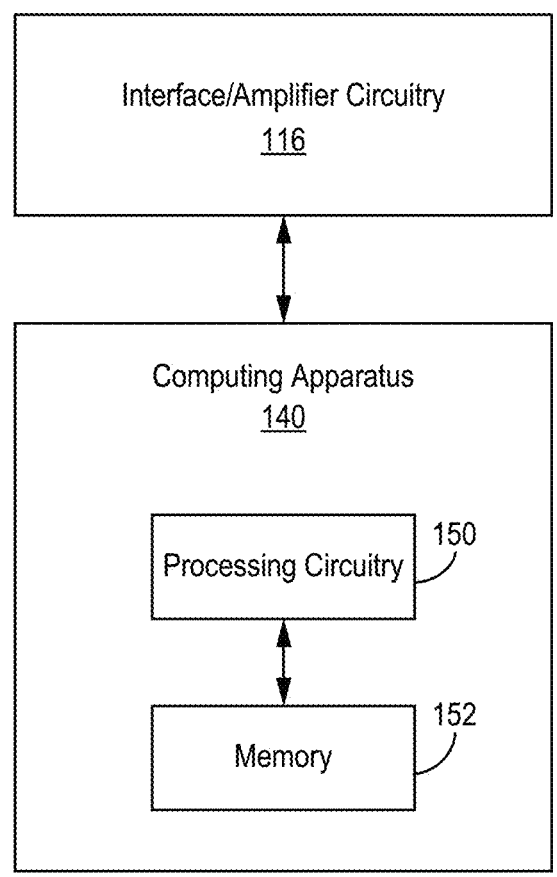
FIG. 4 is a diagram of the interface/amplifier circuitry and the computing apparatus of FIGS. 2-3.

FIG. 4 is a diagram of the interface/amplifier circuitry 116 operatively coupled to the computing apparatus 140. As shown, the computing apparatus 140 may include processing circuitry 150 operatively coupled to memory 152. Each of these components may be used cooperatively to sense electrical activity from the tissue of the patient, such as the patient's heart. For example, the interface/amplifier circuitry 116 may receive electrical activity information measured by a plurality of external electrodes of the electrode apparatus, which may represent sensed electrical activity from the tissue of the patient. The processing circuitry 150 may be used to execute programs stored in the memory 152, for example, to receive the electrical activity information, or data, from the interface/amplifier circuitry 116, to determine a pseudo-electric vector for one or more of the external electrodes, and to generate spatial representation data, or information, of the electrical activity information based on one or more determined pseudo-electric vectors. Such spatial representation data may be used to assist physicians in screening of patients, in the implantation of electrodes, and in programming of a medical device (e.g., a pacemaker).

In general, spatial representation data may be used to represent the electrical forces of the patient's heart. Non-limiting examples of spatial representation data include a plurality of PEVs, combined PEVs, pseudo-vectorcardiography (pseudo-VCG) loops, pseudo-VCG parameters, combinations of these, or visualized models of these. Pseudo-VCG loops and pseudo-VCG parameters may be generated, or determined, using PEVs representing one or more complexes (e.g., QRS complex or T-wave complex). Non-limiting examples of pseudo-VCG loops include a QRS loop or a T-wave loop formed. Non-limiting examples of pseudo-VCG parameters include an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T-wave axis, a dispersion value of the QRS loop, and a dispersion value of the T-wave loop. Non-limiting examples of dispersion values to measure the variability of QRS or T-wave loops is the standard deviation of the distances between consecutive QRS or T-wave loops or the standard deviation of the areas or other geometric parameter of QRS or T-wave loops captured at different times.

A T-wave axis represents the forces of ventricular repolarization in 3D. A QRS axis represents forces of ventricular depolarization in 3D.

The processing circuitry 150 described herein may include a processor, such as a central processing unit (CPU), computer, logic array, or other device capable of directing data coming into or out of the computing apparatus 140. The computing apparatus 140, or even processing circuitry 150, may include one or more computing devices having memory, processing, and communication hardware. The computing apparatus 140 may also be described as a controller. The controller may include circuitry used to couple various components of the controller together or with other components operably coupled to the controller. The functions of the controller may be performed by hardware and/or as computer instructions on a non-transient computer readable storage medium.

A processor of the controller may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, the processor may include multiple components, such as any combination of one or more microprocessors, one or more controllers, one or more DSPs, one or more ASICs, and/or one or more FPGAs, as well as other discrete or integrated logic circuitry. The functions attributed to the controller or processor herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, and interfaces may be implemented using one or more computer programs using a computing apparatus, which may include one or more processors and/or memory. Program code and/or logic described herein may be applied to input data/information to perform functionality described herein and generate desired output data/information. The output data/information may be applied as an input to one or more other devices and/or methods as described herein or as would be applied in a known fashion. In view of the present disclosure, it will be readily apparent that the controller functionality as described herein may be implemented in any manner known to one skilled in the art.

Figure 5:
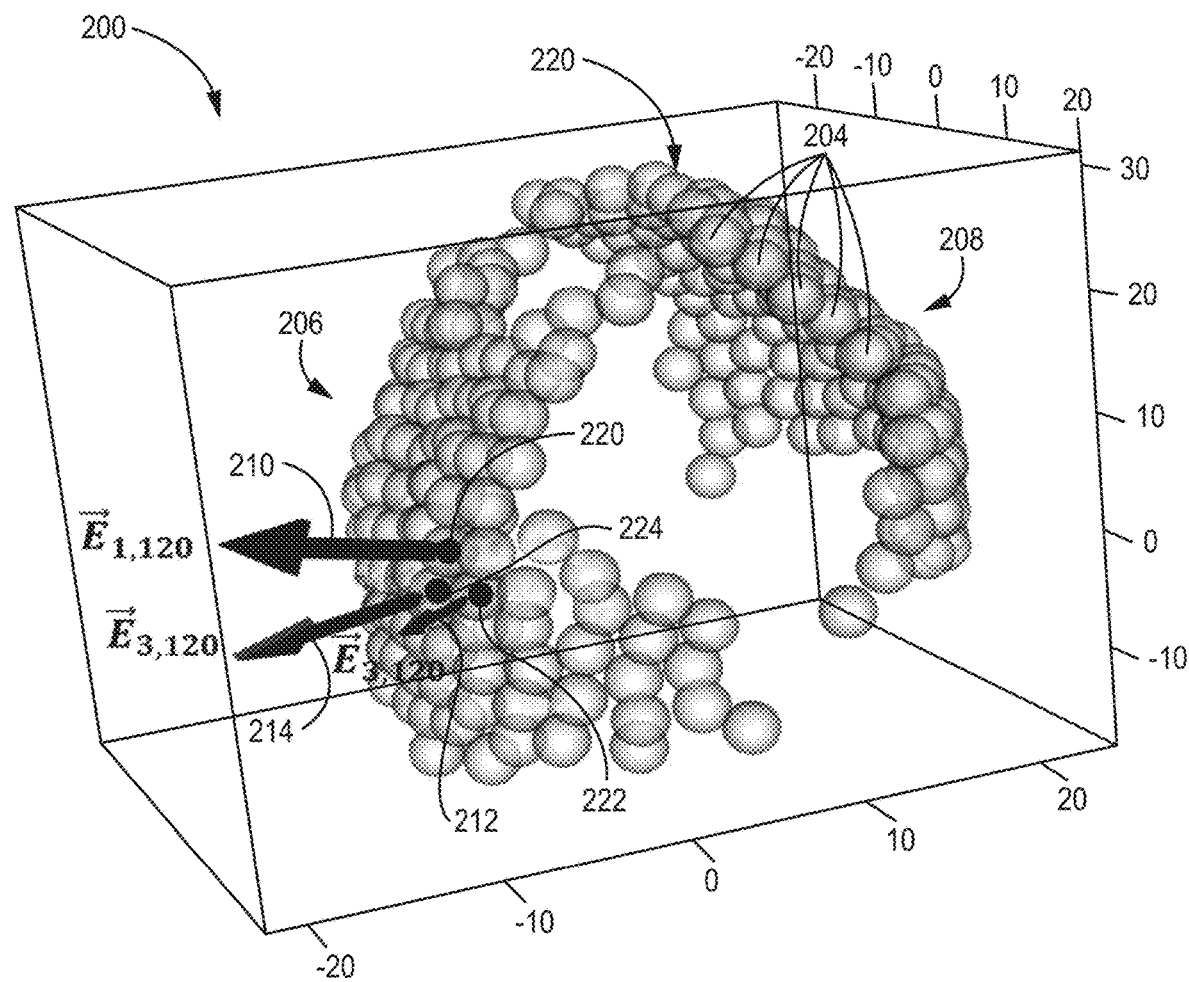
FIG. 5 is a visualized model of electrical activity of a patient's heart showing pseudo-electric vectors (PEVs) generated using, e.g., the system and apparatus of FIGS. 1-4.

FIG. 5 shows a visualized model 200 of electrical activity of the patient's heart. An electrode apparatus 202 is visualized as a cluster of spheres. Each sphere may represent one sensor 204, or external electrode. For example, external electrodes may be part of a belt, vest, or other external electrode apparatus. A belt may also be referred to as a strap in some cases. One example of the electrode apparatus 202 is the ECG vest 114 of FIG. 3.

The electrode apparatus 202 may extend at least partially around the patient (not shown) when the apparatus is worn. One portion of the electrode apparatus 202 may be worn on a front side 206 of the patient, and another portion of the electrode apparatus may be worn on a back side 208 of the patient. In some embodiments, the electrode apparatus 202 may have the same number of sensors 204 near, or on, the front side 206 and the back side 208 (e.g., an even distribution between the front and back). In other embodiments, the electrode apparatus 202 may have a different number of sensors 204 near, or on, the front side 206 compared to the back side 208 (e.g., an uneven distribution between the front and back). In some embodiments, the sensors 204 may be evenly distributed between the front and back at least near the left side of the patient's torso.

In some embodiments, the electrode apparatus 202 may be arranged into one or more rows extending at least partially around the patient. For example, the electrode apparatus 202 may include one, two, three, or more rows of electrodes on the front side 206 and/or back side 208 of the patient. Reducing the number of sensors 204 in the electrode apparatus 202 may provide for simpler calculations and the use of less expensive equipment. In some embodiments, the number of sensors 204 may be less than or equal to 40, 20, or even 10.

A pseudo-electric vector (PEV) ($\vec{E}$), such as PEVs 210, 212, and 214, may be calculated, or determined, based on electrical activity sensed by the electrode apparatus 202. The PEV may be calculated based on measurements by external electrodes. The external electrodes may be fixed, or substantially fixed, relative to a coordinate system of the heart. Once determined, the PEV may be used to estimate an electrical potential on the surface of the patient's heart without a computed tomography (CT) scan and/or computing an inverse solution. In contrast, other systems may use CT scan data to reconstruct the heart and may use an inverse solution to reconstruct the surface of the heart, which can be time consuming and expensive.

In general, the inverse solution is performed by a projection of potentials measured on the surface of the body onto the surface of the heart derived either from a computer model or from patient-specific anatomic images obtained through medical imaging modalities (e.g., echo, MRI, CT, etc.). Various techniques for calculating an inverse solution are described, for example, in U.S. Patent Application Publication No. 2017/0246460, filed Apr. 29, 2016, entitled "Methods and systems of optimizing right ventricular only pacing for patients with respect to an atrial event and left ventricular event."

For a plurality of an array of sensors 204 (e.g., an array of external electrodes) in an electrode apparatus 202, the PEV at time j and on sensor i ($\vec{E}_{ij}$) may be defined as a function of the potential (voltage) on sensor i at time j ($\varphi_{ij}$) and the distance from the sensor i to the heart's center ($\vec{r}_i$). A mathematical definition of $\vec{E}_{ij}$ is shown in Equation 1.

$$\vec{E}_{ij} = f(\varphi_{ij}, \vec{r}_i) \tag{1}$$

where $\vec{r}_i$ is defined as the distance from the sensor i to the center of the patient's heart. A mathematical definition of $\vec{r}_i$ is shown in Equation 1.1.

$$\vec{r}_i = \vec{r}_{sensor\ i} - \vec{r}_{HeartCenter} \tag{1.1}$$

An estimate of the center of the patient's heart may be determined, for example, from imaging data from various imaging modalities (e.g., MRI) used to delineate the pericardium surface of the patient's heart. In some embodiments, a grid or coordinate system may be defined based on the imaging data to provide a 3D model of the patient's heart. Various parts of the patient's heart may be annotated in the grid or coordinate system based on the imaging data. The centroid of the heart may be calculated and used as the heart's center.

The vector $\vec{r}_i$ has the same direction of a line that connects the center of the patient's heart with the sensor i. FIG. 5 illustrates three examples of different PEVs, a first PEV 210, a second PEV 212, and a third PEV 214, each associated with a different a different sensor (e.g., electrode), a first sensor 220, a second sensor 222, and a third sensor 224.

Equation 1 defines $\vec{E}_{ij}$ as a function of $\varphi_{ij}$ and $\vec{r}_i$. In some embodiments, the function used to determine $\vec{E}_{ij}$ may be a scalar product. A mathematical definition of $\vec{E}_{ij}$ is shown in Equation 1.2.

$$\vec{E}_{ij} = \varphi_{ij} \cdot \vec{r}_i \tag{1.2}$$

The magnitude of E that originates the potential $\varphi$ observed at sensor i may depend on the distance from the sensor i to the heart's center ($\vec{r}_i$). The bigger the distance between the sensor i to the heart's center ($\vec{r}_i$), the smaller the potential may be seen due to attenuation. Using a scalar product may compensate for at least some of this attenuation.

Further, the time of arrival of the potential to every sensor, may depend on the distance from the sensor to the heart. Thus, the timing j of the $\vec{E}_{ij}$ on sensor i may be adjusted based on the distance from the sensor i to the center of the patient's heart ($\vec{r}_i$). In other words, the timing j may be different than the timing associated with the potential observed ($\varphi_{ij}$) for each sensor i.

In contrast to other methods, propagation patterns methods of the present disclosure provide a representation (e.g., the PEV) that relates the potential measured by the sensors 204 to directions relative to the center of the heart, instead of only to the timing of potential measured, to characterize the electrical forces of the heart. In some embodiments, propagation patterns methods that use a PEV may be used to predict interventricular dyssynchrony of the heart as shown, for example, in FIGS. 6-13.

Further, a plurality of PEVs may be combined to provide a final vector (e.g., combined PEV) that may be easier for a clinician to interpret, which are discussed hereinbelow in more detail. These final vectors may provide a dynamic representation of electrical forces over time by means of trajectories on the epicardium surface.

Figure 6:
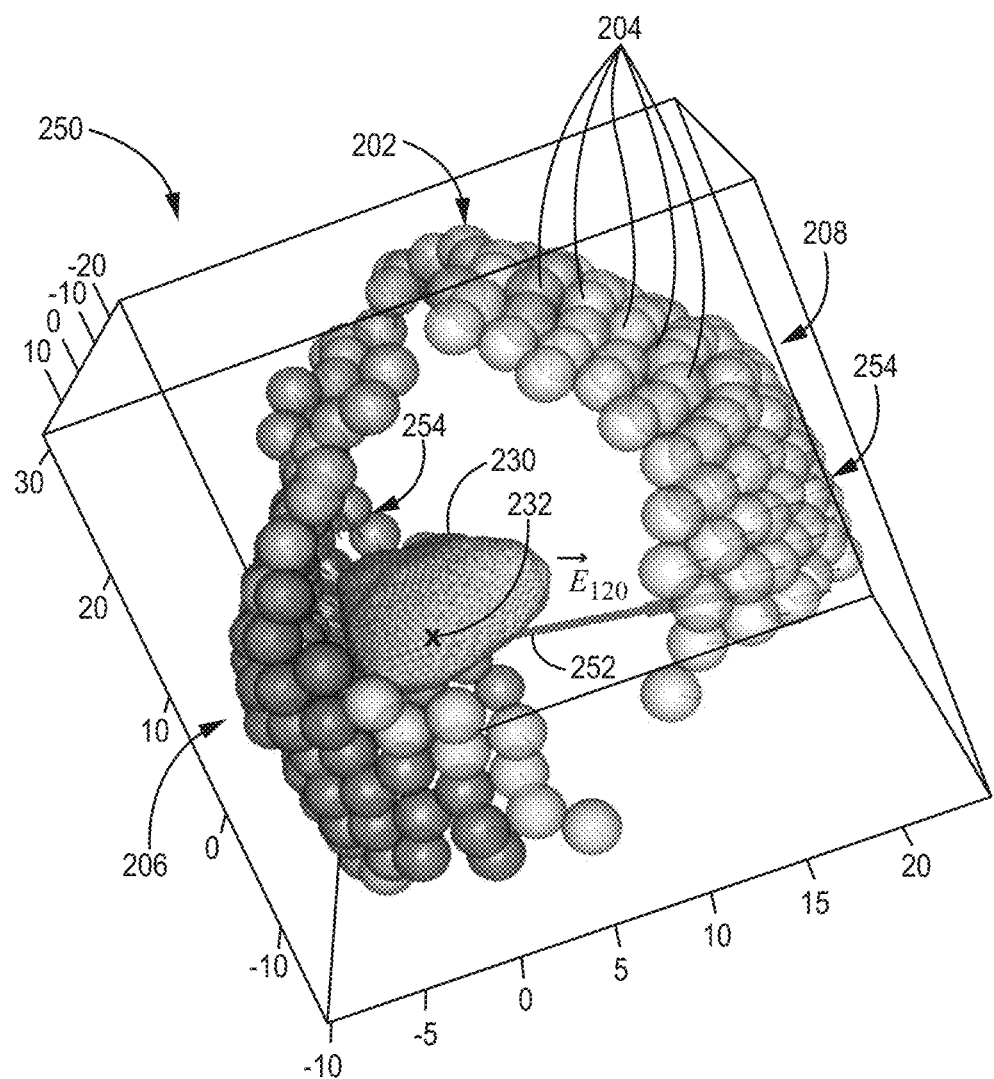
FIG. 6 is a visualized model of electrical activity of a patient's heart showing a sensor-integrated PEV generated using, e.g., the system and apparatus of FIGS. 1-4.

FIG. 6 shows a visualized model 250 of electrical activity of the patient's heart 230 including an estimated center 232 of the patient's heart using the electrode apparatus 202 and a combined PEV 252. As illustrated, a PEV 254 is calculated for each sensor 204 of the electrode apparatus 202, which is represented as a line extending from each sphere representing the sensor (e.g., external electrode). Because the PEVs 254 are based on the potential measured and the direction from the center 232 of the heart, some of the PEVs near the front side 206 point toward the center of the heart (e.g., indicating a negative potential), and other PEVs near the back side 208 point away from the center of the heart (e.g., indicating a positive potential). Further, because the PEVs 254 are based on the distance to the center 232 of the heart, the PEVs near the back side 208 are larger relative to the PEVs near the front side 206, even if the potentials are equal.

A plurality of PEVs may be collected to provide a visualized model, such as visualized model 200 or 250. In some embodiments, a PEV may be determined for some or all the sensors 204 (e.g., for a reduced set of the sensors or for each of the sensors, respectively). In some embodiments, PEVs may be determined for more than one point in time. For example, PEVs may be measured at some or all the sensors 204 at a sampling rate of 1 kHz or any other suitable rate to capture electrical forces of the heart. The plurality of PEVs may be combined in various manners, for example, over a number of sensors and/or over time, to provide different spatial representation data.

In some embodiments, a combined PEV may be a combination of two or more PEVs each associated with a different sensor (e.g., external electrode) of the electrode apparatus 202. In some embodiments, a combined PEV may be determined by combining PEVs 254 by integration, summation, or averaging over the number of sensors n to provide a sensor-integrated PEV. In the illustrated embodiment, the combined PEV 252 is a sensor-integrated PEV, which starts at the center 232 of the heart 230 and extends generally toward the back side 208. The combined PEV 252, as shown, may indicate that the aggregate of the electrical forces at a particular time are generally pointing from the front side 206 toward the back side 208. A mathematical definition of a sensor-integrated PEV determined by summation or integration (e.g., a space-integrated PEV) is shown in Equation 2.

$$\vec{E}_j = \Sigma_{i=1}^n \vec{E}_{ij} \vec{r}_i \qquad (2)$$

Integrated or summed PEVs 254 may be averaged to provide space-average PEVs. A mathematical definition of space-average PEV is shown in Equation 2.1.

$$\vec{E}_j = \frac{\sum_{i=1}^n \vec{E}_{ij} \vec{r}_i}{n} \qquad (2.1)$$

In some embodiments, when the electrode apparatus 202 has the same number of sensors 204 near the front side 206 and the back side 208, all the PEVs 254 may be combined in aggregate (e.g., a total summation, integration, or averaging). In other embodiments, when the electrode apparatus 202 has a different number of sensors 204 near the front side 206 compared to the back side 208, the PEVs 254 associated with the front side 206 and back side 208 may be averaged separately (e.g., into partial sensor-integrated PEVs), and then the two averaged PEVs may be averaged together to arrive at a final combined PEV (e.g., a total sensor-integrated PEV). Other techniques that would be known to a person having skill in the art having the benefit of the present disclosure may also be used to balance the front side 206 versus the back side 208 when there are different numbers of sensors 204.

Figure 7A:
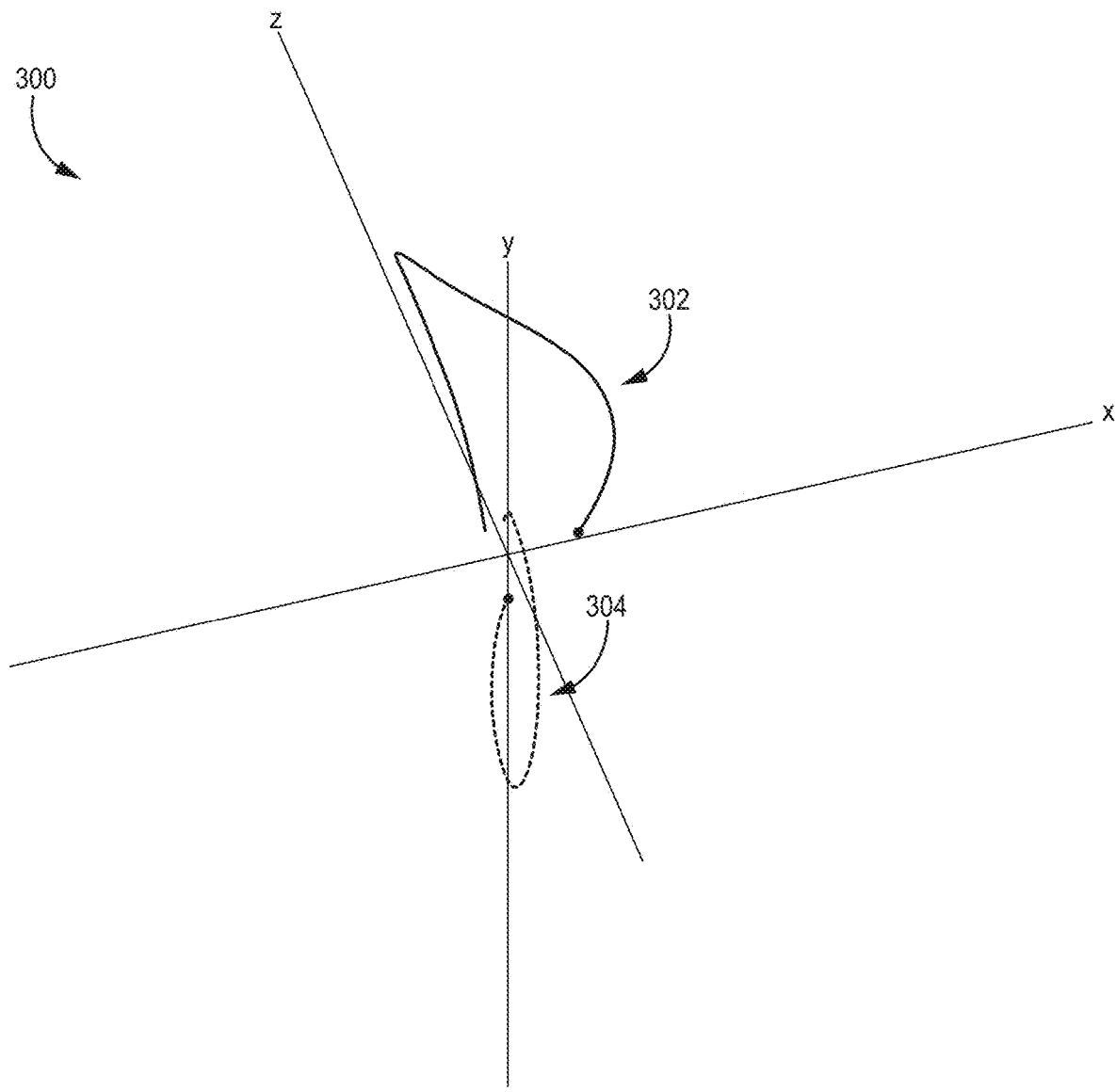
FIGS. 7A-B are visualized models of electrical activity of a patient's heart showing pseudo-vectorcardiography (VCG) loops generated using, e.g., the system and apparatus of FIGS. 1-4.

FIG. 7A shows a visualized model 300 representing a plurality of combined PEVs as loops 302, 304, such as pseudo-VCG loops representing the QRS complex or the T-wave complex. The QRS loop 302 represents electrical activity information for the QRS complex. The T-wave loop 304 represents electrical activity information for the T-wave complex. Each loop represents the endpoint of combined PEVs at different points in time and illustrates how the electrical forces change over time.

In general, the QRS complex represents the depolarization of the ventricles of the patient's heart. The T-wave complex represents the repolarization of the ventricles of the patient's heart. The P-wave complex represents the depolarization of the atrium of the patient's heart.

One or more pseudo-VCG parameters may be determined based on combined PEVs. In particular, one or more pseudo-VCG parameters may be determined based on a plurality of combined PEVs that represent loops. For example, a pseudo-VCG parameter, such as an area of the T-wave loop or an average vector of the T-wave loop, may be calculated based on a plurality of combined PEVs, such as a plurality of sensor-integrated PEVs.

In some embodiments, a combined PEV may be a combination of two or more PEVs each associated with a different time. For example, a combined PEV may be determined by combining PEVs by integration, summation, or averaging over the number of time samples m to provide a time-integrated PEV. In particular, the time-integrated PEV may be a combination of a plurality of sensor-integrated PEVs 252. Each sensor-integrated PEV may be associated with a different time value. In some embodiments, the time-integrated PEV determined by integration or summation may be averaged to provide a time-average PEV. A mathematical definition of a time-integrated PEV is shown in Equation 3.

$$\vec{E} = \frac{\sum_{j=1}^m \vec{E}_j}{m} = \frac{\sum_{j=1}^m \sum_{i=1}^n \vec{E}_{ij}}{n \cdot m} \qquad (3)$$

Figure 7B:
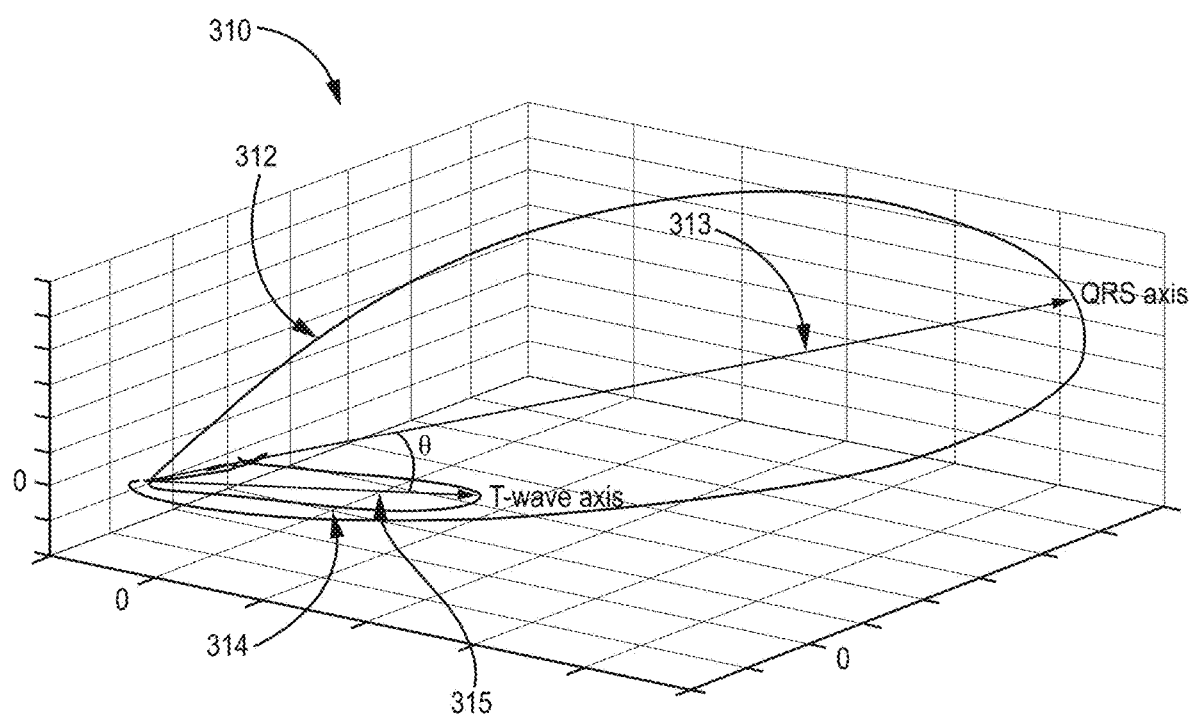
Figure 8:
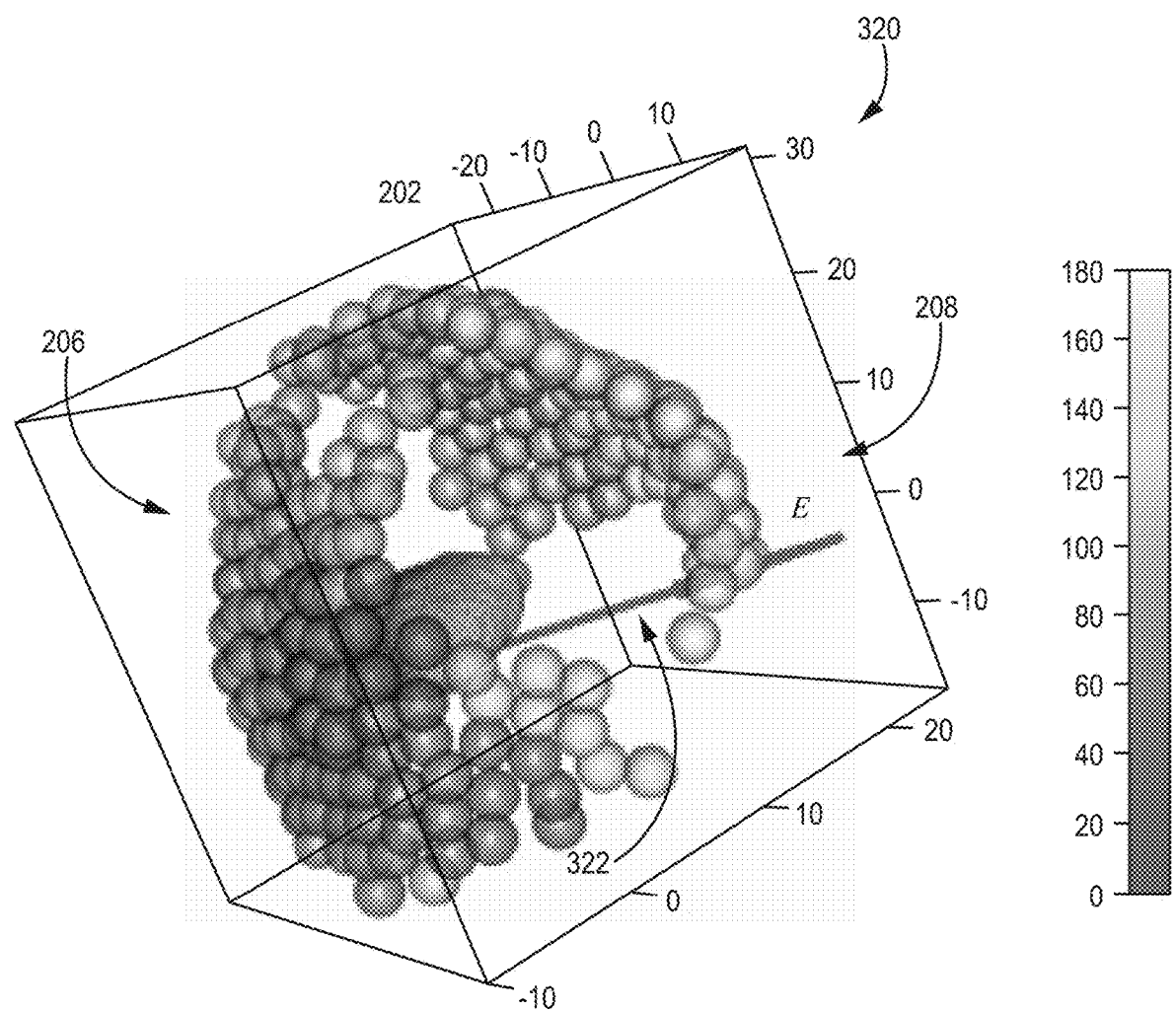
FIG. 8 is a visualized model of electrical activity of a patient's heart showing a time-integrated PEV generated using. e.g., the system and apparatus of FIGS. 1-4.

FIG. 7B shows a visualized model 310 representing a plurality of combined PEVs as loops 312, 314, such as pseudo-VCG loops representing the QRS complex or the T-wave complex. The QRS loop 312 represents electrical activity information for the QRS complex formed using a combined QRS PEV 313, such as a sensor-integrated PEV corresponding to the QRS complex. The combined QRS PEV 313 may be described as a QRS axis. The T-wave loop 304 represents electrical activity information for the T-wave complex formed using a combined T-wave PEV 315, such as a sensor-integrated PEV corresponding to the T-wave complex. The combined T-wave PEV 315 may be described as a T-wave axis. A three-dimensional spatial angle θ may be defined between the combined QRS PEV 313 and the combined T-wave PEV 315.

From a combined PEV ($\vec{E}$), relevant information may be determined, such as the effect of different types of pacing on the electrical forces of the heart. As shown in FIGS. 8-13, different time-integrated PEVs are illustrated that are generated based on a pacing sequence from intrinsic conduction to an atrioventricular delay of 200 ms (AVD200) with a left ventricular delay of 30 ms (LV30) for a patient. For the case of the intrinsic rhythm, as shown in the visualized model 320 of FIG. 8, the combined PEV ($\vec{E}$) 322 is pointing to the back side 208 indicating that the propagation goes from the front side 206 (e.g., right ventricle or RV) to the back side 208 (e.g., left ventricle or LV), which may indicate that the patient has a left bundle branch block (LBBB) because a patient's heart with an LBBB may conduct from the right ventricle to the left ventricle. In the illustrated embodiment, the combined PEV 322 represents the integration of PEVs of the QRS complex over multiple sensors and over a time window (e.g., a time-integrated PEV).

Figure 9:
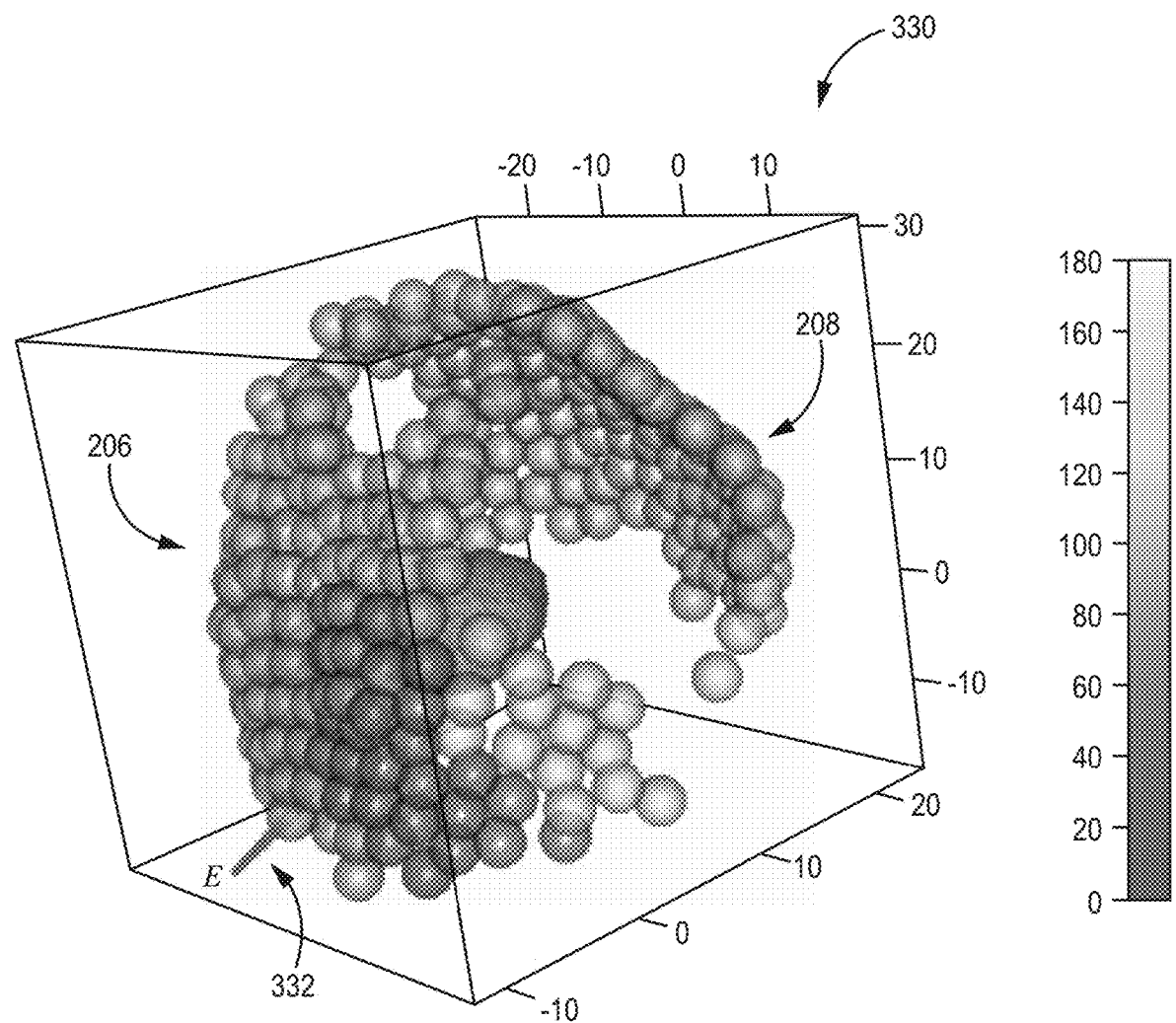
FIGS. 9-13 are visualized models of electrical activity of a patient's heart showing a time-integrated PEV in response to different pacing timing generated using, e.g., the system and apparatus of FIGS. 1-4.

When pacing is provided to the left-side part of the heart tissue (e.g., left ventricle) with AVD100 LV30 as shown in the visualized model 330 of FIG. 9, the combined PEV 332 points in almost the opposite direction as combined PEV 322. In other words, the combined PEV 332 is pointing to the front side 206 indicating that propagation goes from the back side 208 (e.g., LV) to the front side 206 (e.g., RV).

Figure 10:
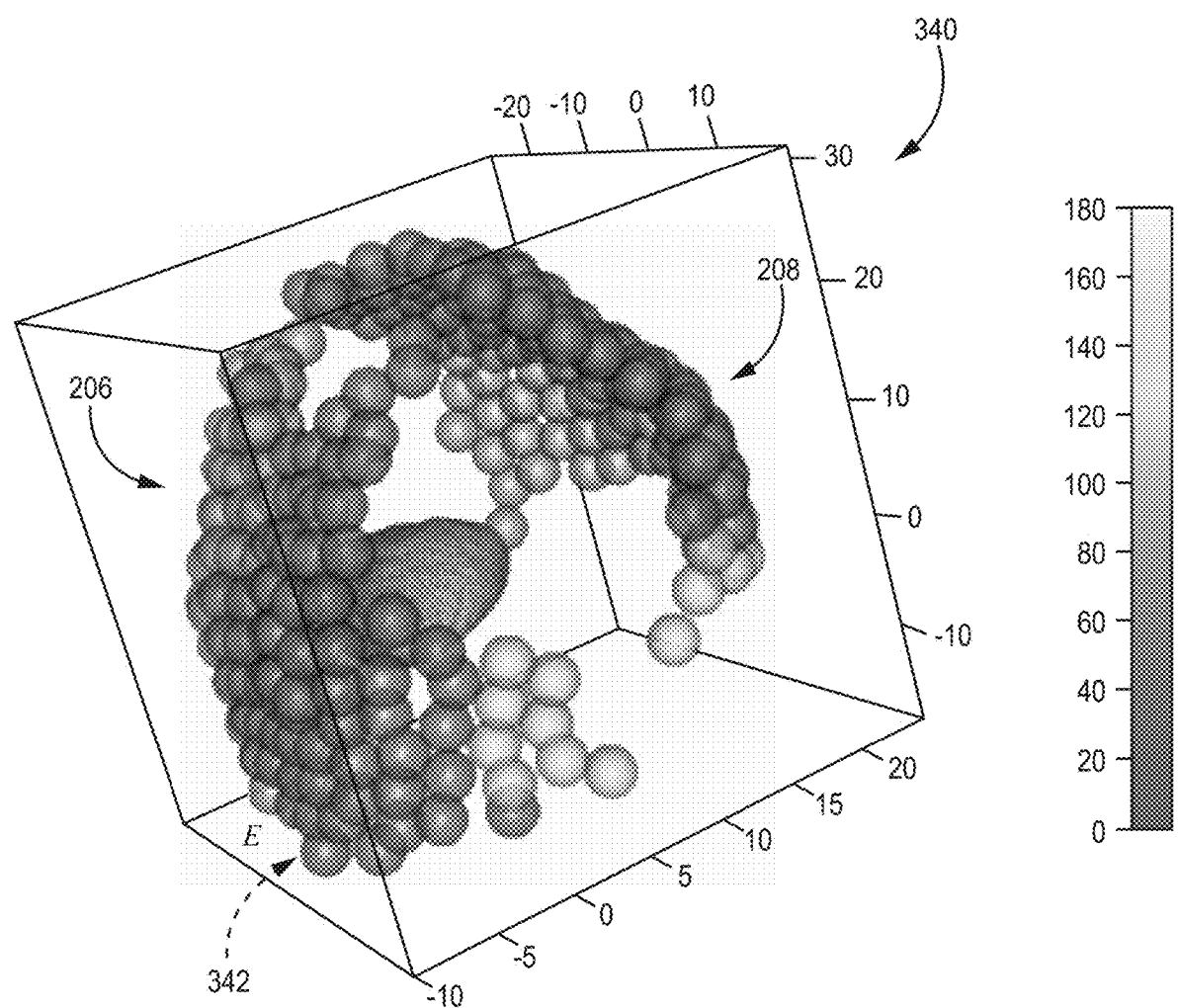
Figure 11:
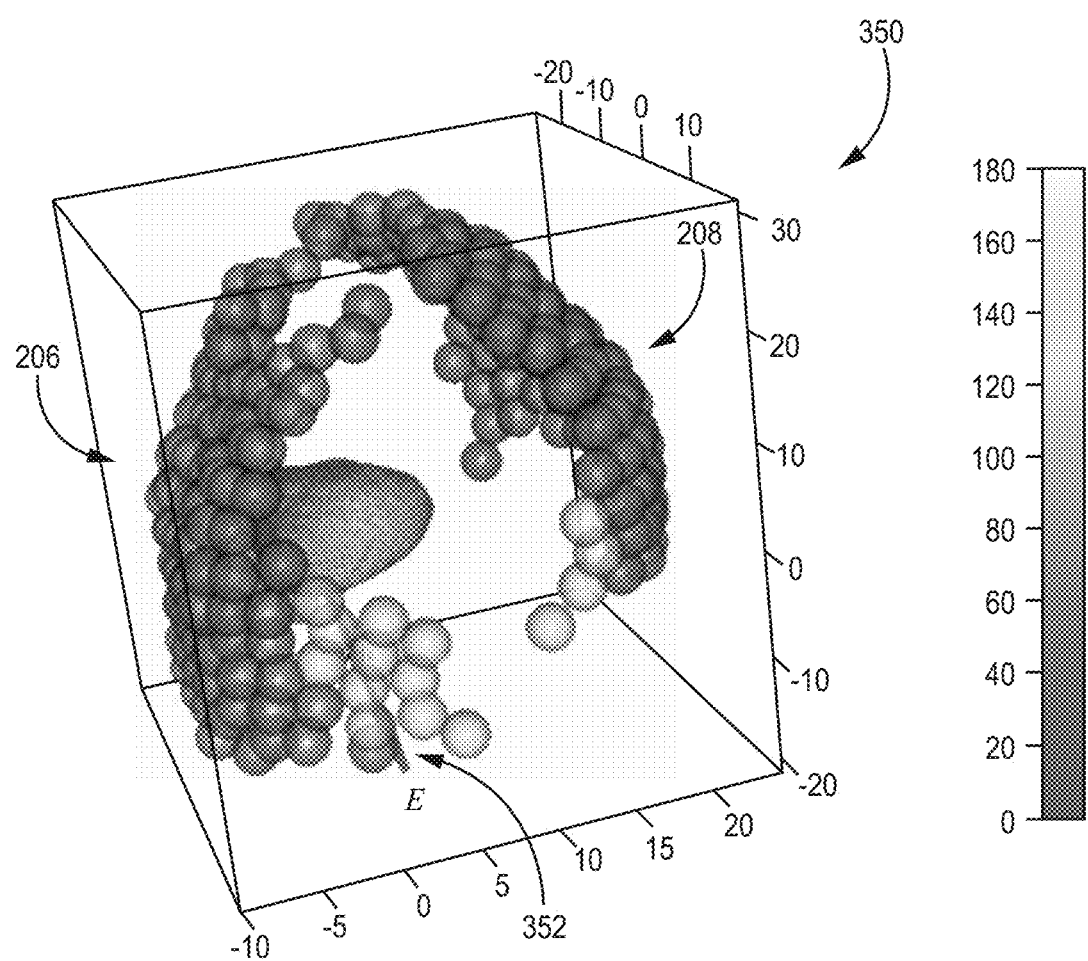

As AVD is increased from FIGS. 9-13, the combined PEVs return, or become more similar, to an intrinsic situation. For example, the visualized model 340 of FIG. 10 represents AVD120 LV30 and shows that the magnitude of the combined PEV 342 may be equal to, or almost equal to zero (and is, therefore, hidden in this perspective view). The visualized model 350 of FIG. 11 represents AVD140 LV30 and shows that the combined PEV 342 is pointing in a direction between the front side 206 and the back side 208 (e.g., in a sideways direction). Visualized models 340, 350 show both the front side 206 and the back side 208 being activated. This may indicate that pacing of the left-side part is taking over intrinsic conduction, which may be desirable in some cases.

Figure 12:
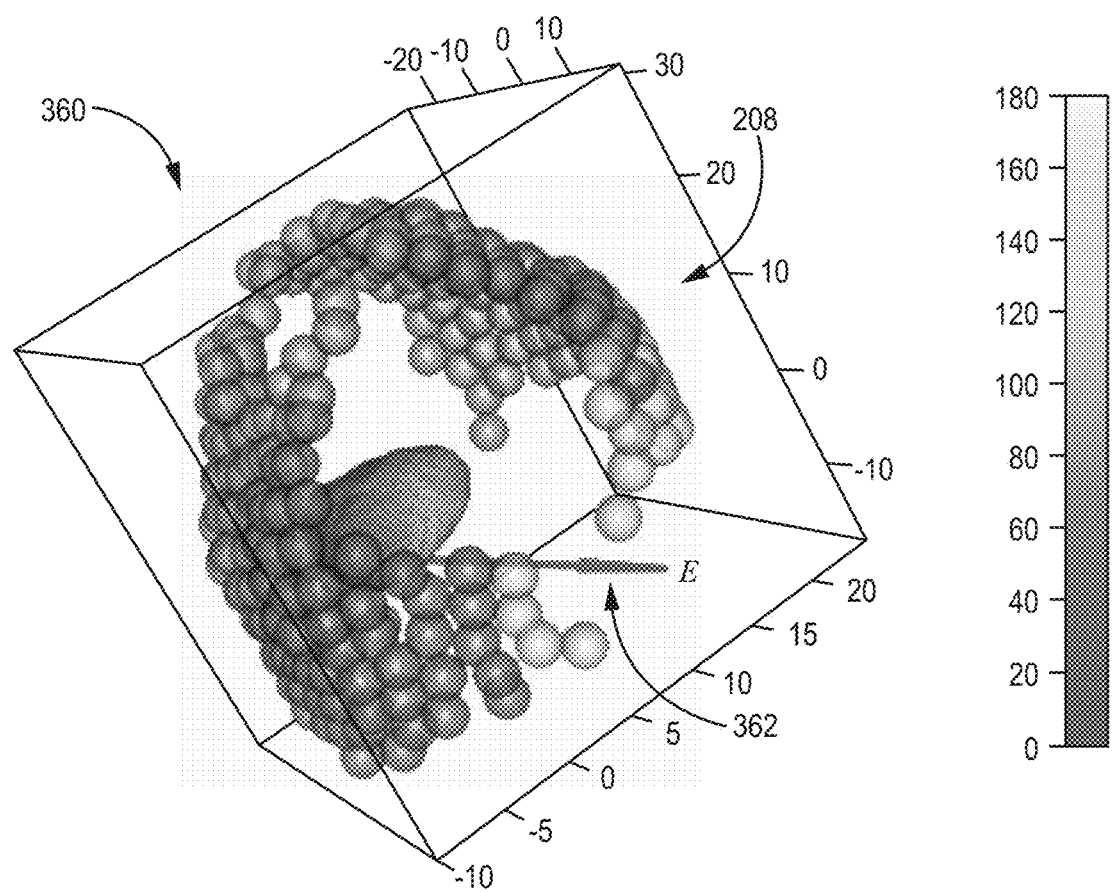
Figure 13:
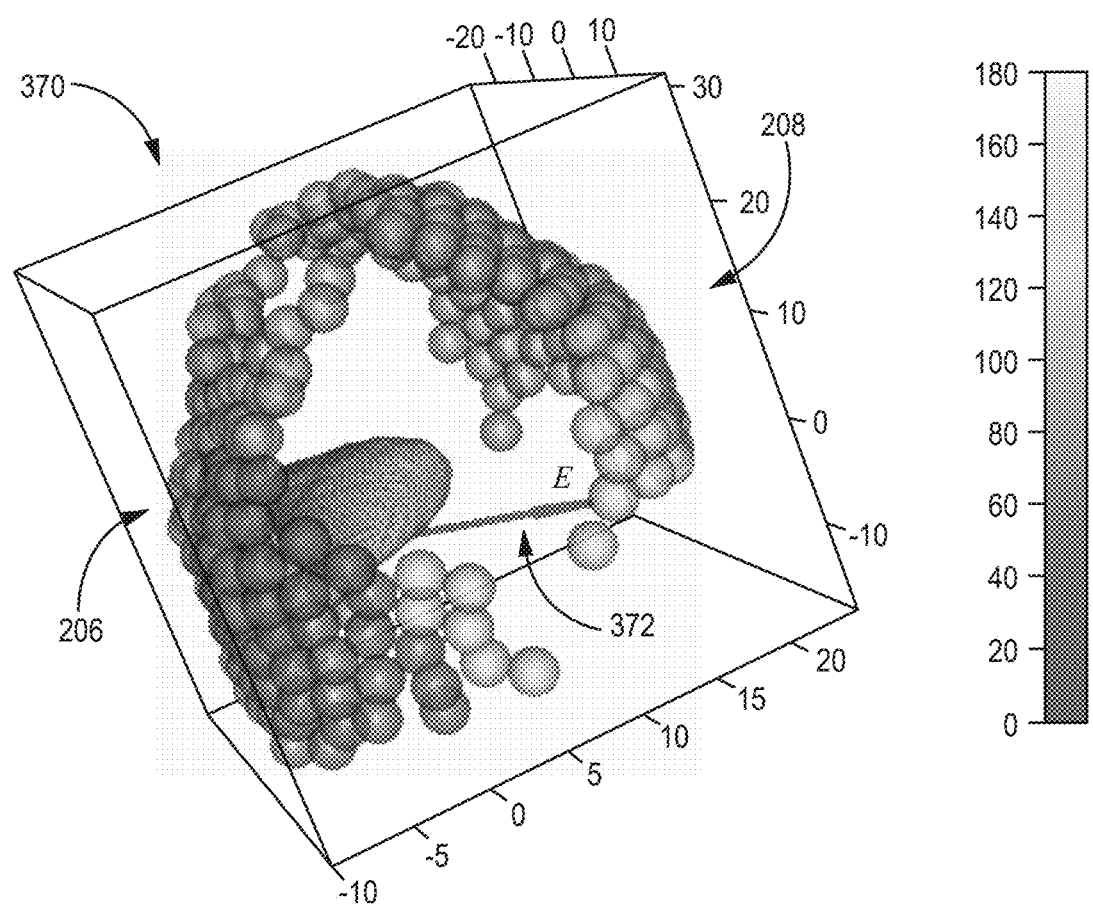

The visualized model 360 of FIG. 12 represents AVD160 LV30 and shows that the combined PEV 362 is pointing more toward the back side 208 than the combined PEV 352 of FIG. 11. The visualized model 370 of FIG. 13 represents AVD200 LV30 and shows that the combined PEV 372 is pointing even more toward the back side 208 than the combined PEV 362 of FIG. 12. The combined PEV 372 may be similar to the combined PEV 322 of FIG. 8 in direction and magnitude, for example, because the LV may have already been paced by the RV through intrinsic conduction before the left-side part is paced. The combined PEV 372 may be somewhat smaller than the combined PEV 322 due to some contribution from pacing the left-side part.

In general, FIGS. 8-13 show that a combined PEV may provide information about electrical activation of the surface of the patient's heart. For example, the combined PEVs may be used to determine interventricular dyssynchrony (e.g., by estimating an interventricular delay), to predict a patient's response to CRT (e.g., by predicting a long-term CRT response using pseudo-VCG loops), to provide optimal lead location, or to provide optimal device programming or reprogramming.

In some embodiments, PEVs or combined PEVs may be used to determine interventricular dyssynchrony. For example, some electrodes of the electrode apparatus may be selected and associated with the RV (e.g., front side) and other electrodes of the electrode apparatus may be selected and associated with the LV (e.g., back side). The PEVs for these electrodes may be averaged and used as an estimate for the activation times of the RV and LV. The estimated activation times may be subtracted from one another (e.g., estimated LV activation time minus estimated RV activation time) to determine an interventricular delay.

In some embodiments, PEVs or combined PEVs may be used to select patients that will respond to CRT who may not have a typical LBBB condition. For example, the long-term CRT response for a patient may be predicted using pseudo-VCG loops. The pseudo-VCG loops may provide a measure of loop, area or other geometric indices corresponding to depolarization (QRS), repolarization (T), and combined depolarization and repolarization (QRST), which may be used to predict the long-term CRT response when the baseline value of these measures exceeds a certain threshold or is bound by certain thresholds.

In some embodiments. PEVs or combined PEVs may be used to provide optimal lead location and/or optimal device programming during implant, for example, using changes in measurements based on PEV during pacing relative to baseline values. In particular, a baseline measurement of the PEV loops may be taken before the patient receives a pacing device. During implant, a physician may test potential implantation sites for a pacing device. The PEV loops at each potential implantation site may be compared with the baseline measurements to determine which potential implantation site to use, for example, because the PEV loops comparison indicates a potential response to therapy at that site. Once the implantation site is selected, different programming of the pacing device may be tested and the PEV loops may be measured and compared to the baseline measurements to determine which programming to use.

In some embodiments, PEVs or combined PEVs may be used to provide optimal device reprogramming after implant, for example, during follow-up appointments with a clinician. Due to an implanted pacing device, the heart may be adapting to therapy (e.g., remodeling). The pacing device may be reprogrammed to find optimal programming for the current state of the patient's heart. Different programming of the pacing device may be tested and the PEV loops may be measured and compared to the baseline measurements (e.g., from before implantation) to determine which programming to use.

Figure 14:
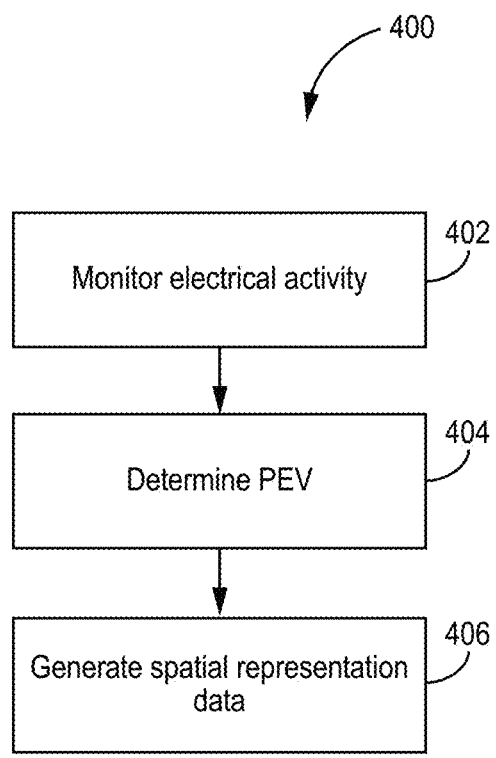
FIG. 14 is a diagram showing one example of a method of using PEVs generated using, e.g., the system and apparatus of FIGS. 1-4.

FIG. 14 is a diagram showing one example of a method 400 for using PEVs. The method 400 may include sensing electrical activity 402, for example, using a plurality of sensors (e.g., external electrodes). The method 400 may also include determining a PEV 404, for example, for one or more of the sensors based on an estimated center of the patient's heart and the sensed electrical activity. At least one PEV may be determined for each of the sensors in the plurality of sensors or for a reduced set of sensors in the plurality of sensors. The method 400 may further include generating spatial representation data 406, for example, of the sensed electrical activity based on the one or more the determined pseudo-electric vectors.

Figure 15:
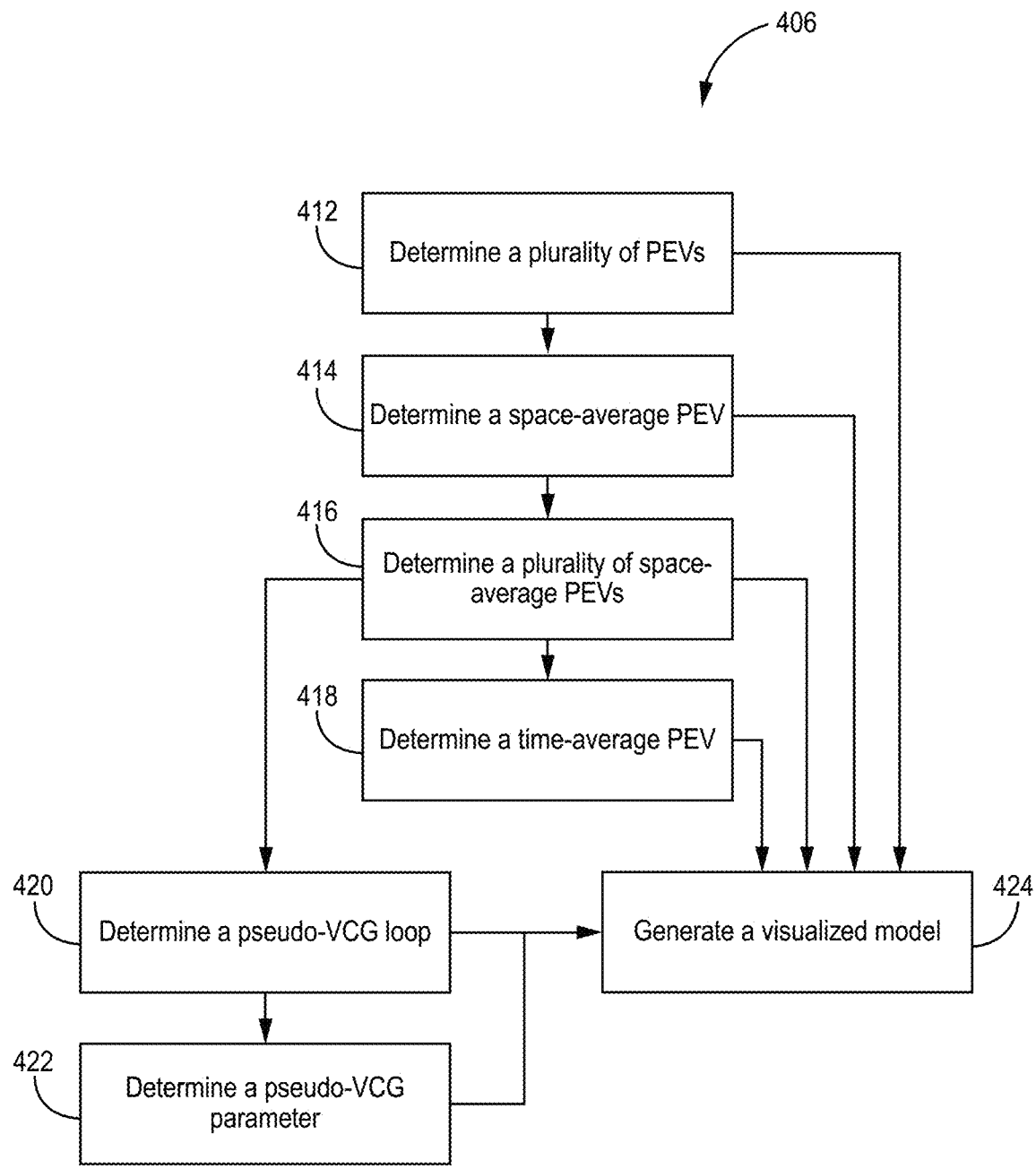
FIG. 15 is a diagram showing one example of a method of generating spatial representation data using, e.g., the system and apparatus of FIGS. 1-4.

FIG. 15 is a diagram showing one example of a method 406 of generating spatial representation data and possible relationships between the data. The method 406 may include determining a plurality of PEVs 412, for example, using multiple sensors and/or at multiple points in time. The method 406 may include determining a sensor-integrated PEV 414, for example, based on a combination of two or more PEVs each associated with a different sensor of the plurality of sensors.

Method 406 may include determining a plurality of sensor-integrated PEVs 416, for example, with each sensor-integrated PEV being associated with a different time value (e.g., at different points in time). Method 406 may also include determining a time-integrated PEV 418, for example, based on a combination of two or more sensor-integrated PEVs with each sensor-integrated PEV being associated with a different time value.

Method 406 may include determining a pseudo-VCG loop 420 and/or a pseudo-VCG parameter 422, for example, based on one or more sensor-integrated PEVs. Various loops and parameters may be determined, for example, as described hereinabove.

Method 406 may also include generating a visualized model 424 based on PEVs or combined PEVs. For example, visualized models may be generated based on one or more of: a PEV, a plurality of PEVs, a sensor-integrated PEV, a plurality of sensor-integrated PEVs, a time-integrated PEV, a pseudo-VCG loop, or a pseudo-VCG parameter.

While the present disclosure is not so limited, an appreciation of various aspects of the disclosure will be gained through a discussion of the specific illustrative embodiments provided below. Various modifications of the illustrative embodiments, as well as additional embodiments of the disclosure, will become apparent herein.

ILLUSTRATIVE EMBODIMENTS

In illustrative embodiment A1, a cardiac sensing system comprises electrode apparatus comprising a plurality of external electrodes to sense electrical activity from tissue of a patient and computing apparatus comprising processing circuitry operatively coupled to the electrode apparatus. The processing circuitry is configured to: sense electrical activity using the plurality of external electrodes; determine a pseudo-electric vector for one or more of the external electrodes based on an estimated center of the patient's heart and the sensed electrical activity; and generate spatial representation data of the sensed electrical activity based on the one or more determined pseudo-electric vectors.

In illustrative embodiment A2, a system comprises a system according to embodiment A1, wherein the processing circuitry is further configured to determine a sensor-integrated pseudo-electric vector based on a combination of two or more pseudo-electric vectors each associated with a different external electrode of the plurality of external electrodes.

In illustrative embodiment A3, a system comprises a system according to embodiment A2, wherein the processing circuitry is further configured to determine a pseudo-VCG parameter based on the sensor-integrated pseudo-electric vector.

In illustrative embodiment A4, a system comprises a system according to embodiment A3, wherein the pseudo-VCG parameter represents one or more of: an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T axis, a dispersion value of the QRS loop, and a dispersion value of the T-wave loop.

In illustrative embodiment A5, a system comprises a system according to any embodiment A2-A4, wherein the processing circuitry is further configured to generate the spatial representation data of the sensed electrical activity based on a plurality of sensor-integrated pseudo-electric vectors, wherein each sensor-integrated pseudo-electric vector is associated with a different time value.

In illustrative embodiment A6, a system comprises a system according to embodiment A4, wherein the spatial representation data represents one or more of a QRS loop and a T-wave loop.

In illustrative embodiment A7, a system comprises a system according to any A embodiment, wherein the processing circuitry is further configured to determine a time-integrated pseudo-electric vector based on a combination of two or more sensor-integrated pseudo-electric vectors, wherein each sensor-integrated pseudo-electric vector is associated with a different time value.

In illustrative embodiment A8, a system comprises a system according to any A embodiment, wherein the processing circuitry is configured to determine at least one pseudo-electric vector for each of the external electrodes in the plurality the external electrodes.

In illustrative embodiment A9, a system comprises a system according to any embodiment A2-A7, wherein the processing circuitry is configured to determine at least one pseudo-electric vector for a reduced set of external electrodes in the plurality of external electrodes.

In illustrative embodiment B1, a method comprises sensing electrical activity of a patient's heart using a plurality of external electrodes; determining a pseudo-electric vector for one or more of the external electrodes based on an estimated center of the patient's heart and the sensed electrical activity; and generating spatial representation data of the sensed electrical activity based on the one or more the determined pseudo-electric vectors.

In illustrative embodiment B2, a method comprises a method according to embodiment B1, further comprising determining a sensor-integrated pseudo-electric vector based on a combination of two or more pseudo-electric vectors each associated with a different external electrode of the plurality of external electrodes.

In illustrative embodiment B3, a method comprises a method according to embodiment B2, further comprising determining a pseudo-VCG parameter based on the sensor-integrated pseudo-electric vector.

In illustrative embodiment B4, a method comprises a method according to embodiment B3, wherein the pseudo-VCG parameter represents one or more of: an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T axis, a dispersion value of the QRS loop, and a dispersion value of the T-wave loop.

In illustrative embodiment B5, a method comprises a method according to any embodiment B2-B4, further comprising generating the spatial representation data of the sensed electrical activity based on a plurality of sensor-integrated pseudo-electric vectors, wherein each sensor-integrated pseudo-electric vector is associated with a different time value.

In illustrative embodiment B6, a method comprises a method according to embodiment B5, wherein the spatial representation data represents one or more of a QRS loop and a T-wave loop.

In illustrative embodiment B7, a method comprises a method according to any embodiment B2-B6, further comprising determining a time-integrated pseudo-electric vector based on a combination of two or more sensor-integrated pseudo-electric vectors, wherein each sensor-integrated pseudo-electric vector is associated with a different time value.

In illustrative embodiment B8, a method comprises a method according to any B embodiment, wherein determining the pseudo-electric vector comprises determining at least one pseudo-electric vector for each of the external electrodes in the plurality the external electrodes.

In illustrative embodiment B9, a method comprises a method according to any embodiment B1-B7, wherein determining the pseudo-electric vector comprises determining at least one pseudo-electric vector for a reduced set of external electrodes in the plurality of external electrodes.

In illustrative embodiment C1, a system comprises interface circuitry configured to receive electrical activity information measured by a plurality of external electrodes that represents sensed electrical activity from tissue of a patient and processing circuitry operatively coupled to the interface circuitry. The processing circuitry is configured to: receive the electrical activity information; determine a pseudo-electric vector for one or more of the external electrodes based on an estimated center of the patient's heart and the received electrical activity information; and generate spatial representation data of the electrical activity information based on the one or more determined pseudo-electric vectors.

In illustrative embodiment C2, a system comprises a system according to embodiment C1, wherein the processing circuitry is further configured to determine a sensor-integrated pseudo-electric vector based on a combination of two or more pseudo-electric vectors each associated with a different external electrode of the plurality of external electrodes.

In illustrative embodiment C3, a system comprises a system according to embodiment C2, wherein the processing circuitry is further configured to determine a pseudo-VCG parameter based on the sensor-integrated pseudo-electric vector.

In illustrative embodiment C4, a system comprises a system according to embodiment C3, wherein the pseudo-VCG parameter represents one or more of: an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T axis, a dispersion value of the QRS loop, and a dispersion value of the T-wave loop.

In illustrative embodiment C5, a system comprises a system according to any embodiment C2-C4, wherein the processing circuitry is further configured to generate the spatial representation data of the electrical activity information based on a plurality of sensor-integrated pseudo-electric vectors, wherein each sensor-integrated pseudo-electric vector is associated with a different time value.

In illustrative embodiment C6, a system comprises a system according to embodiment C5, wherein the spatial representation data represents one or more of a QRS loop and a T-wave loop.

In illustrative embodiment C7, a system comprises a system according to any embodiment C2-C6, wherein the processing circuitry is further configured to determine a time-integrated pseudo-electric vector based on a combination of two or more sensor-integrated pseudo-electric vectors, wherein each sensor-integrated pseudo-electric vector is associated with a different time value.

In illustrative embodiment C8, a system comprises a system according to any C embodiment, wherein the processing circuitry is configured to determine at least one pseudo-electric vector for each of the external electrodes in the plurality the external electrodes.

In illustrative embodiment C9, a system comprises a system according to any embodiment C1-C7, wherein the processing circuitry is configured to determine at least one pseudo-electric vector for a reduced set of external electrodes in the plurality of external electrodes.

Thus, various embodiments of PROPAGATION PATTERNS METHOD AND RELATED SYSTEMS AND DEVICES are disclosed. Various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect incorporated directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g., 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out at least some functionality (for example, a first medical device may be operatively coupled to another medical device to transmit information in the form of data or to receive data therefrom).

Terms related to orientation, such as "top," "bottom," "side," and "end," are used to describe relative positions of components and are not meant to limit the orientation of the embodiments contemplated. For example, an embodiment described as having a "top" and "bottom" also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all the listed elements or a combination of at least two of the listed elements.

The phrases "at least one of," "comprises at least one of," and "one or more of" followed by a list refers to any one of the items in the list and any combination of two or more items in the list.

The invention claimed is:

1. A cardiac modeling system comprising:
   an electrode apparatus comprising a plurality of external electrodes to sense electrical activity from tissue of a patient;
   a display apparatus configured to display generated three-dimensional spatial visualized models of electrical activity of the patient's heart; and
   a computing apparatus comprising processing circuitry operatively coupled to the electrode apparatus and configured to:
      sense electrical activity at a singular time value using the plurality of external electrodes;
      determine two or more three-dimensional pseudo-electric vectors for the singular time value, where each three-dimensional pseudo-electric vector is based on an estimated center of the patient's heart and the sensed electrical activity of one of the external electrodes of the plurality of external electrodes;
      generate a three-dimensional spatial visualized model of electrical activity of the patient's heart comprising two or more three-dimensional pseudo-electric vector graphical representations, each three-dimensional pseudo-electric vector graphical representation graphically depicting a potential and a direction of one of the two or more determined three-dimensional pseudo-electric vectors; and
      update the three-dimensional spatial visualized model of electrical activity of the patient's heart in real time based on a different singular time value; and
      display the updated three-dimensional spatial visualized model of electrical activity of the patient's heart on the display apparatus.

2. The system of claim 1, wherein the processing circuitry is further configured to determine a sensor-integrated pseudo-electric vector based on a combination of two or more three-dimensional pseudo-electric vectors of the two or more determined three-dimensional pseudo-electric vectors.

3. The system of claim 2, wherein the processing circuitry is further configured to determine a pseudo-vectorcardiography parameter based on the sensor-integrated pseudo-electric vector.

4. The system of claim 3, wherein the pseudo-vectorcardiography parameter represents one or more of: an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T axis, a dispersion value of the QRS loop, and a dispersion value of the T-wave loop.

5. The system of any one of claims 2-4, wherein the processing circuitry is further configured to:
sense electrical activity at a plurality of time values using the plurality of external electrodes;
determine a plurality of three-dimensional pseudo-electric vectors by determining two or more three-dimensional pseudo-electric vectors for each time value of the plurality of time values, where each three-dimensional pseudo-electric vector is based on the estimated center of the patient's heart and the sensed electrical activity of one of the external electrodes of the plurality of external electrodes; and
determine a plurality of sensor-integrated pseudo-electric vectors by determining a sensor-integrated pseudo-electric vector for each time value of the plurality of time values, where each sensor-integrated pseudo-electric vector is based on a combination of two or more three-dimensional pseudo-electric vectors of the two or more determined three-dimensional pseudo-electric vectors,
wherein generating the three-dimensional spatial visualized model of electrical activity of the patient's heart is further based on the plurality of sensor-integrated pseudo-electric vectors.

6. The system of claim 5, wherein the three-dimensional spatial visualized model of electrical activity of the patient's heart represents one or more of a QRS loop and a T-wave loop.

7. The system of claim 2, wherein the processing circuitry is further configured to:
sense electrical activity at a plurality of time values using the plurality of external electrodes;
determine a plurality of three-dimensional pseudo-electric vectors by determining two or more three-dimensional pseudo-electric vectors for each time value of the plurality of time values, where each three-dimensional pseudo-electric vector is based on the estimated center of the patient's heart and the sensed electrical activity of one of the external electrodes of the plurality of external electrodes;
determine a plurality of sensor-integrated pseudo-electric vectors by determining a sensor-integrated pseudo-electric vector for each time value of the plurality of time values, where each sensor-integrated pseudo-electric vector is based on a combination of two or more three-dimensional pseudo-electric vectors of the determined two or more three-dimensional pseudo-electric vectors; and
determine a time-integrated pseudo-electric vector based on a combination of two or more sensor-integrated pseudo-electric vectors of the plurality of sensor-integrated pseudo-electric vectors,
wherein generating the three-dimensional spatial visualized model of electrical activity of the patient's heart is further based on the time-integrated pseudo-electric vector.

8. The system of claim 1, wherein the two or more three-dimensional pseudo-electric vectors for the singular time value comprises at least one three-dimensional pseudo-electric vector for each external electrode of the external electrodes in the plurality the external electrodes.

9. The system of claim 1, wherein the two or more three-dimensional pseudo-electric vectors for the singular time value comprises at least one three-dimensional pseudo-electric vector for each external electrode of a reduced set of external electrodes in the plurality of external electrodes.

10. The system of claim 1, wherein the displayed three-dimensional spatial visualized model of electrical activity of the patient's heart is configured to be manipulatable by a user using the display apparatus.

11. A method comprising:
sensing electrical activity of a patient's heart at a singular time value using a plurality of external electrodes;
determining two or more three-dimensional pseudo-electric vectors for the singular time value, where each three-dimensional pseudo-electric vector is based on an estimated center of the patient's heart and the sensed electrical activity of one of the external electrodes of the plurality of external electrodes;
generating a three-dimensional spatial visualized model of electrical activity of the patient's heart comprising two or more three-dimensional pseudo-electric vector graphical representations, each three-dimensional pseudo-electric vector graphical representation graphically depicting a potential and a direction of one of the two or more determined three-dimensional pseudo-electric vectors;
updating the three-dimensional spatial visualized model of electrical activity of the patient's heart in real time based on a different singular time value; and
displaying the updated three-dimensional spatial visualized model of electrical activity of the patient's heart using a display apparatus.

12. The method of claim 11, further comprising determining a sensor-integrated pseudo-electric vector based on a combination of two or more three-dimensional pseudo-electric vectors of the two or more determined three-dimensional pseudo-electric vectors.

13. The method of claim 12, further comprising determining a pseudo-vectorcardiography parameter based on the sensor-integrated pseudo-electric vector.

14. The method of claim 13, wherein the pseudo-vectorcardiography parameter represents one or more of: an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T axis, a dispersion value of the QRS loop, and a dispersion value of the T-wave loop.

15. The method of any one of claims 12-14, further comprising:
sensing electrical activity of the patient's heart at a plurality of time values using the plurality of external electrodes;
determining a plurality of three-dimensional pseudo-electric vectors by determining two or more three-dimensional pseudo-electric vectors for each time value of the plurality of time values, where each three-dimensional pseudo-electric vector is based on the estimated center of the patient's heart and the sensed electrical activity of one of the external electrodes of the plurality of external electrodes; and
determining a plurality of sensor-integrated pseudo-electric vectors by determining a sensor-integrated pseudo-electric vector for each time value of the plurality of time values, where each sensor-integrated pseudo-electric vector is based on a combination of two or more three-dimensional pseudo-electric vectors of the determined two or more three-dimensional pseudo-electric vectors;
wherein generating the three-dimensional spatial visualized model of electrical activity of the patient's heart is further based on the determined plurality of sensor-integrated pseudo-electric vectors.

16. The method of claim 15, wherein the three-dimensional spatial visualized model of electrical activity of the patient's heart represents one or more of a QRS loop and a T-wave loop.

17. The method of claim 12, further comprising:
sensing electrical activity of the patient's heart at a plurality of time values using the plurality of external electrodes;
determining a plurality of three-dimensional pseudo-electric vectors by determining two or more three-dimensional pseudo-electric vectors for each time value of the plurality of time values, where each three-dimensional pseudo-electric vector is based on the estimated center of the patient's heart and the sensed electrical activity of one of the external electrodes of the plurality of external electrodes;
determining a plurality of sensor-integrated pseudo-electric vectors by determining a sensor-integrated pseudo-electric vector for each time value of the plurality of time values, where each sensor-integrated pseudo-electric vector is based on a combination of two or more three-dimensional pseudo-electric vectors of the determined two or more three-dimensional pseudo-electric vectors; and
determining a time-integrated pseudo-electric vector based on a combination of two or more sensor-integrated pseudo-electric vectors of the plurality of sensor-integrated pseudo-electric vectors,
wherein generating the three-dimensional spatial visualized model of electrical activity of the patient's heart is further based on the time-integrated pseudo-electric vector.

18. The method of claim 11, wherein the two or more three-dimensional pseudo-electric vectors for the singular time value comprises at least one three-dimensional pseudo-electric vector for each external electrode of the external electrodes in the plurality the external electrodes.

19. The method of claim 11, wherein the two or more three-dimensional pseudo-electric vectors for the singular time value comprises at least one three-dimensional pseudo-electric vector for each external electrode of a reduced set of external electrodes in the plurality of external electrodes.

20. A system comprising:
interface circuitry configured to receive electrical activity information at a singular time value measured by a plurality of external electrodes that represents sensed electrical activity from tissue of a patient;
a display apparatus configured to display generated three-dimensional spatial visualized models of electrical activity of the patient's heart; and
processing circuitry operatively coupled to the interface circuitry and configured to:
receive the electrical activity information;
determine two or more three-dimensional pseudo-electric vectors for the singular time value, where each three-dimensional pseudo-electric vector is based on an estimated center of the patient's heart and the received electrical activity information of one of the external electrodes of the plurality of electrodes;
generate a three-dimensional spatial visualized model of electrical activity of the patient's heart comprising two or more three-dimensional pseudo-electric vector graphical representations, each three-dimensional pseudo-electric vector graphical representation graphically depicting a potential and a direction of one of the two or more determined three-dimensional pseudo-electric vectors;
update the three-dimensional spatial visualized model of electrical activity of the patient's heart in real time based on a different singular time value; and
display the updated three-dimensional spatial visualized model of electrical activity of the patient's heart on the display apparatus.

21. The system of claim 20, wherein the processing circuitry is further configured to determine a sensor-integrated pseudo-electric vector based on a combination of two or more three-dimensional pseudo-electric vectors of the two or more determined three-dimensional pseudo-electric vectors.

22. The system of claim 21, wherein the processing circuitry is further configured to determine a pseudo-vectorcardiography parameter based on the sensor-integrated pseudo-electric vector.

23. The system of claim 22, wherein the pseudo-vectorcardiography parameter represents one or more of: an area of a T-wave loop, an area of a QRS loop, an area of both QRS and T-wave loops, a perimeter of a QRS loop, a perimeter of a T-wave loop, a perimeter of both QRS and T-wave loops, a ratio between area and perimeter of a QRS loop, a ratio between area and perimeter of a T-wave loop, a ratio between area and perimeter of both QRS and T-wave loops, an average vector for a QRS loop, an average vector for a T-wave loop, an average vector of both QRS and T-wave loops, a spatial angle between QRS and T axis, a dispersion value of the QRS loop, and a dispersion value of the T-wave loop.

24. The system of any one of claims 21-23, wherein the processing circuitry is further configured to:
sense electrical activity at a plurality of time values using the plurality of external electrodes;
determine a plurality of three-dimensional pseudo-electric vectors by determining two or more three-dimensional pseudo-electric vectors for each time value of the plurality of time values, where each three-dimensional pseudo-electric vector is based on the estimated center of the patient's heart and the sensed electrical activity of one of the external electrodes of the plurality of external electrodes; and
determine a plurality of sensor-integrated pseudo-electric vectors by determining a sensor-integrated pseudo-electric vector for each time value of the plurality of time values, where each sensor-integrated pseudo-electric vector is based on a combination of two or more three-dimensional pseudo-electric vectors of the two or more determined three-dimensional pseudo-electric vectors,
wherein generating the three-dimensional spatial visualized model of electrical activity of the patient's heart is further based on the plurality of sensor-integrated pseudo-electric vectors.

25. The system of claim 24, wherein the three-dimensional spatial visualized model of electrical activity of the patient's heart represents one or more of a QRS loop and a T-wave loop.

26. The system of claim 21, wherein the processing circuitry is further configured to:

sense electrical activity at a plurality of time values using the plurality of external electrodes;

determine a plurality of three-dimensional pseudo-electric vectors by determining two or more three-dimensional pseudo-electric vectors for each time value of the plurality of time values, where each three-dimensional pseudo-electric vector is based on the estimated center of the patient's heart and the sensed electrical activity of one of the external electrodes of the plurality of external electrodes;

determine a plurality of sensor-integrated pseudo-electric vectors by determining a sensor-integrated pseudo-electric vector for each time value of the plurality of time values, where each sensor-integrated pseudo-electric vector is based on a combination of two or more three-dimensional pseudo-electric vectors of the determined two or more three-dimensional pseudo-electric vectors; and determine a time-integrated pseudo-electric vector based on a combination of two or more sensor-integrated pseudo-electric vectors of the plurality of sensor-integrated pseudo-electric vectors, wherein generating the three-dimensional spatial visualized model of electrical activity of the patient's heart is further based on the time-integrated pseudo-electric.

27. The system of claim 20, wherein the two or more three-dimensional pseudo-electric vectors for the singular time value comprises at least one three-dimensional pseudo-electric vector for each external electrode of the external electrodes in the plurality the external electrodes.

28. The system of claim 20, wherein the two or more three-dimensional pseudo-electric vectors for the singular time value comprises at least one three-dimensional pseudo-electric vector for each external electrode of a reduced set of external electrodes in the plurality of external electrodes.

* * * * *